(12) United States Patent
Lipani

(10) Patent No.: US 10,773,100 B2
(45) Date of Patent: Sep. 15, 2020

(54) TREATMENT OF UNRUPTURED SACCULAR INTRACRANIAL ANEURYSMS USING STEREOTACTIC RADIOSURGERY

(71) Applicant: John D. Lipani, New Hope, PA (US)

(72) Inventor: John D. Lipani, New Hope, PA (US)

(*) Notice: Subject to any disclaimer, the term of this patent is extended or adjusted under 35 U.S.C. 154(b) by 186 days.

(21) Appl. No.: 15/663,724

(22) Filed: Jul. 29, 2017

(65) Prior Publication Data

US 2019/0030368 A1 Jan. 31, 2019

(51) Int. Cl.
*A61N 5/10* (2006.01)
*A61B 90/10* (2016.01)
*A61B 17/00* (2006.01)

(52) U.S. Cl.
CPC ............ *A61N 5/1031* (2013.01); *A61B 90/10* (2016.02); *A61N 5/1084* (2013.01); *A61B 2017/00778* (2013.01); *A61B 2090/101* (2016.02); *A61N 5/1039* (2013.01); *A61N 5/1049* (2013.01); *A61N 5/1075* (2013.01); *A61N 2005/1035* (2013.01); *A61N 2005/1041* (2013.01); *A61N 2005/1052* (2013.01); *A61N 2005/1055* (2013.01); *A61N 2005/1087* (2013.01)

(58) Field of Classification Search
CPC .......... A61N 2005/1087; A61N 5/1031; A61N 5/1084; A61N 5/10; A61N 5/00
See application file for complete search history.

(56) References Cited

U.S. PATENT DOCUMENTS

| | | |
|---|---|---|
| 6,931,096 B2 | 8/2005 | Carlsson |
| 6,968,036 B2 | 11/2005 | Carlsson |
| 7,313,222 B2 | 12/2007 | Carlsson |
| RE42,756 E | 9/2011 | Guglielmi |
| 8,221,435 B2 | 7/2012 | Arndt |
| 2001/0001806 A1* | 5/2001 | Turnlund ......... A61B 17/12113 600/3 |
| 2009/0306483 A1 | 12/2009 | Garding |

(Continued)

FOREIGN PATENT DOCUMENTS

WO   WO-2008040522 A2 *  4/2008 ........... A61N 5/1031

OTHER PUBLICATIONS

Van Gijn J, Kerr RS, Rinkel GJ. Subarachnoid haemorrhage. Lancet 369 (9558, 2007): 306-318.

(Continued)

*Primary Examiner* — Christine H Matthews
(74) *Attorney, Agent, or Firm* — David R. Rigney

(57) ABSTRACT

Methods and devices are disclosed for treating a patient with an unruptured saccular aneurysm that is not associated with an arteriovenous malformation, wherein ionizing radiation is delivered to the brain of a patient through stereotactic radiosurgery. The radiosurgery may be performed with a Gamma Knife stereotactic radiosurgery apparatus, LINAC device such as CYBERKNIFE® stereotactic radiosurgery apparatus, or particle-beam device. The treatment impedes a natural progression of the aneurysm towards rupture and may actually obliterate the aneurysm. The treatment plan may be based in part on measured geometric properties of the aneurysm or on physical aneurysm properties such as permeability, wall thickness, wall motion, the presence of macrophages, shear stress, and flow velocities. The methods may be used in conjunction with endovascular coil embolization.

17 Claims, 4 Drawing Sheets

(56) References Cited

U.S. PATENT DOCUMENTS

| | | | | |
|---|---|---|---|---|
| 2011/0160513 | A1* | 6/2011 | Luan | A61N 5/103 600/1 |
| 2013/0047103 | A1* | 2/2013 | Avisar | G09B 23/28 715/764 |
| 2015/0208994 | A1* | 7/2015 | Rapoport | G01R 33/4812 600/411 |
| 2018/0192916 | A1* | 7/2018 | De Man | A61B 8/0891 |

OTHER PUBLICATIONS

Hae Woong Jeong, Jung Hwa Seo, Sung Tae Kim, Cheol Kyu Jung, and Sang-il Suh. Clinical practice guideline for the management of intracranial aneurysms. Neurointervention 9(2014):63-71.

Nader-Sepahi A, Casimiro M, Sen J, Kitchen ND. Is aspect ratio a reliable predictor for intracranial aneurysm rupture? Neurosurgery 54(6,2004):1343-1348.

Ujiie H, Tachibana H, Hiramatsu O, Hazel AL, Matsumoto T, et al. Effects of size and shape (aspect ratio) on the hemodynamics of saccular aneurysms: a possible index for surgical treatment of intracranial aneurysms. Neurosurgery 45(1,1999):119-130.

Kassell NF, Torner JC. Size of intracranial aneurysms. Neurosurgery 12(1983):291-297.

Hunt WE, Hess RM. Surgical risk as related to time of intervention in the repair of intracranial aneurysms. J Neurosurg 28(1968):14-20.

Frontera JA, Claassen J, Schmidt JM, Wartenberg KE, Temes R, Connolly ES Jr, MacDonald RL, Mayer SA. Prediction of symptomatic vasospasm after subarachnoid hemorrhage: the modified fisher scale. Neurosurgery 59(1,2006)21-27.

Ogilvy, Christopher S. and Carter, Bob S. A Proposed Comprehensive Grading System to Predict Outcome for Surgical Management of Intracranial Aneurysms. Neurosurgery 42(5, 1998):959-968.

Khanna RK, Malik GM, Qureshi N: Predicting outcome following surgical treatment of unruptured intracranial aneurysms: A proposed grading system. J Neurosurg 84(1996):49-54.

Solomon RA, Fink ME, Pile-Spellman J: Surgical management of unruptured intracranial aneurysms. J Neurosurg 80(1994):440-446.

Sonobe M, Yamazaki T, Yonekura M, Kikuchi H. Small unruptured intracranial aneurysm verification study: SUAVe study, Japan. Stroke 41(2010):1969-1977.

Polevaya NV, Kalani MY, Steinberg GK, Tse VC. The transition from hunterian ligation to intracranial aneurysm clips: a historical perspective. Neurosurg Focus 20 (6,2006):E3, pp. 1-7.

Nicola Acciarri, Giovanni Toniato, Andreas Raabe, and Giuseppe Lanzion. Clipping techniques in cerebral aneurysm surgery. Journal of Neurological Sciences 60(1, 2016):83-94.

Harley Brito Da Silva, Mario Messina-Lopez, and Laligam N. Sekhar. Bypasses and Reconstruction for Complex Brain Aneurysms. Methodist Debakey Cardiovasc J. 10(4,2014): 224-233.

Brad Seibert, Ramachandra P. Tummala, Ricky Chow, Alireza Faridar, Seyed A. Mousavi and Afshin A. Divani. Intracranial aneurysms: review of current treatment options and outcomes. Frontiers in Neurology 2(45,Jul. 2011), doi: 10.3389/fneur.2011.00045, pp. 1-11.

I.Y.L. Tan, R.F. Agid, and R.A. Willinsky. Recanalization rates after endovascular coil embolization in a cohort of matched ruptured and unruptured cerebral aneurysms. Interv Neuroradiol. 17(1,2011):27-35.

Pietro I. D'Urso, Giuseppe Lanzino, Harry J. Cloft and David F. Kallmes. Flow Diversion for Intracranial Aneurysms : A Review. Stroke 42(2011):2363-2368.

Adam M. Brouillard, Xingwen Sun, Adnan H. Siddiqui, Ning Lin. The use of flow diversion for the treatment of intracranial aneurysms: expansion of indications. Cureus 8(1): e472. DOI 10.7759/cureus.472. pp. 1-8.

Kulcsar Z, Houdart E, Bonafé A et al. Intra-aneurysmal thrombosis as a possible cause of delayed aneurysm rupture after flow-diversion treatment. AJNR Am J Neuroradiol. 32(1,2011):20-25.

Michael T. Lawton, W. Caleb Rutledge, Helen Kim, et al. Brain arteriovenous malformations. Nature Reviews Disease Primers 1, Article No. 15008 (2015) doi:10.1038/nrdp.2015.8, pp. 1-20.

Esther J. Kim, Sandra Vermeulen, Francisco J. Li, David W. Newell. A review of cerebral arteriovenous malformations and treatment with stereotactic radiosurgery. Transl Cancer Res 3(4, 2014):399-410.

Chang SD, Shuster DL, Steinberg GK, Levy RP, Frankel K: Stereotactic radiosurgery of arteriovenous malformations: Pathologic changes in resected tissue. Clin Neuropathol 16(1997):111-116.

Timothy D. Solberg, Robert L. Siddon, and Brian Kavanagh. Historical Development of Stereotactic Ablative Radiotherapy. pp. 9-35 In: S. S. Lo et al. (eds.), Stereotactic Body Radiation Therapy, Medical Radiology. Berlin and Heidelberg: Springer-Verlag, 2012.

L. Dade Lunsford, Ajay Niranjan, Douglas Kondziolka, Sait Sirin and J.C. Flickinger. Arteriovenous Malformation Radiosurgery: A Twenty Year Perspective. Clinical Neurosurgery 55(2008):108-119.

A. Niranjan, L.D. Lunsford, J.C. Flickinger, J. Novotny, J. Bhatnager, and D. Kondziolka. Gamma Knife: Clinical Experience. Chapter 66 in: Textbook of Stereotactic and Functional Neurosurgery, vol. 1 (Andres M. Llano, Philip L. Gildenberg, and Ronald R. Tasker, eds.) Berlin: Springer, 2009. p. 1071.

Steiner L. Radiosurgery in cerebral arteriovenous malformations. In: Fein JM and Flamm E, editor. Cerebrovascular surgery, vol. 4. New York: Springer-Verlag, 1985. pp. 1161-1215, at pp. 1209-1210.

Lars Leksell. Stereotactic radiosurgery. Journal of Neurology, Neurosurgery, and Psychiatry 46(1983):797-803.

Lan Z, Li J, You C, Chen J. Successful use of Gamma Knife surgery in a distal lenticulostriate artery aneurysm intervention. Br J Neurosurg 26(1,2012):89-90.

Choi C-Y, Han S-R, Yee G-T, Lee C-H. Spontaneous regression of an unruptured and non-giant intracranial aneurysm. Journal of Korean Neurosurgical Society. 52(3,2012):243-245.

Jayakumar PN, Ravishankar S, Balasubramaya KS, Chavan R, Goyal G. Disappearing saccular intracranial aneurysms: do they really disappear? Interventional Neuroradiology 13(3,2007):247-254.

Raymond J, Mounayer C, Salazkin I, Metcalfe A, Gevry G, Janicki C, Roorda S, Leblanc P. Safety and effectiveness of radioactive coil embolization of aneurysms: effects of radiation on recanalization, clot organization, neointima formation, and surrounding nerves in experimental models. Stroke 37(8,2006):2147-2152.

Gary H. Gibbons, and Victor J. Dzau. The Emerging Concept of Vascular Remodeling. N Engl J Med 330(1994):1431-1438.

Herity NA, Ward MR, Lo S, Yeung AC. Review: Clinical aspects of vascular remodeling. J Cardiovasc Electrophysiol. 10(7,1999):1016-1024.

Nanney AD 3rd, El Tecle NE, El Ahmadieh TY, Daou MR, Bit Ivan EN, Marymont MH, Batjer HH, Bendok BR. Intracranial aneurysms in previously irradiated fields: literature review and case report. World Neurosurg 81(3-4,2014):511-519.

Sales literature for Leksell Gamma Knife® Perfexion™ (Catalog No. 715000), Elekta Instrument AB, Box 7593, Tungsten 18, SE-103 93 Stockholm, Sweden.

Sales literature for Leksell GammaPlan® for Perfexion™ (Catalog No. 1006938), Elekta Instrument AB, Box 7593, Tungsten 18, SE-103 93 Stockholm, Sweden.

Neuroscience Products and Services Catalog of Elekta Instrument AB, Box 7593, Tungsten 18, SE-103 93 Stockholm, Sweden, pp. 87-98.

Seung SK, Larson DA, Galvin JM, Mehta MP, Potters L, Schultz CJ, Yajnik SV, Hartford AC, Rosenthal SA. American College of Radiology (ACR) and American Society for Radiation Oncology (ASTRO) Practice guideline for the performance of stereotactic radiosurgery (SRS). Am J Clin Oncol. 36(3,2013):310-315.

Vakil P, Ansari SA, Cantrell CG, Eddleman CS, Dehkordi FH, Vranic J, et al. Quantifying intracranial aneurysm wall permeability for risk assessment using dynamic contrast-enhanced MRI: A pilot study. AJNR Am J Neuroradiol 36(2015):953-959.

Kleinloog R, Korkmaz E, Zwanenburg JJ, Kuijf HJ, Visser F, Blankena R, et al. Visualization of the aneurysm wall: a 7.0-tesla magnetic resonance imaging study. Neurosurgery 75(2014):614-622.

(56) References Cited

OTHER PUBLICATIONS

Vanrossomme AE, Eker OF, Thiran JP, Courbebaisse GP, Zouaoui Boudjeltia K. Intracranial aneurysms: Wall motion analysis for prediction of rupture. AJNR Am J Neuroradiol 36(2015):1796-1802.
Juan R Cebral, Mariano Vazquez, Daniel M Sforza, Guillaume Houzeaux, Satoshi Tateshima, Esteban Scrivano, Carlos Bleise, Pedro Lylyk, Christopher M Putman. Analysis of hemodynamics and wall mechanics at sites of cerebral aneurysm rupture. J Neurointerv Surg 7(2015):530-536.
Schnell S, Ansari SA, Vakil P, Wasielewski M, Carr ML, Hurley MC, et al. Three dimensional hemodynamics in intracranial aneurysms: influence of size and morphology. J Magn Reson Imaging 39(2014):120-131.
Boussel L, Rayz V, Martin A, Acevedo-Bolton G, Lawton MT, Higashida R, et al. Phase-contrast magnetic resonance imaging measurements in intracranial aneurysms in vivo of flow patterns, velocity fields, and wall shear stress: comparison with computational fluid dynamics. Magn Reson Med 61(2009):409-417.
Michael R. Levitt, M. Yashar S. Kalani, Karam Moon, Cameron G. McDougall, Felipe C. Albuquerque. Advances in the imaging of cerebral aneurysm inflammation. Neuroimmunol Neuroinflammation 2(2,2015): 51-54.
Tiffany Y. So, Richard Dowling, Peter J. Mitchell, John Laidlaw, Bernard Yan. Risk of growth in unruptured intracranial aneurysms: A retrospective analysis. Journal of Clinical Neuroscience 17(2010):29-33.
Luciana Parlea, Rebecca Fahrig, David W. Holdsworth, and Stephen P. Lownie. An Analysis of the Geometry of Saccular Intracranial Aneurysms. AJNR Am J Neuroradiol 20(1999):1079-1089.
Dengsheng Zhang, Guojun Lu. Review of shape representation and description techniques. Pattern Recognition 37(2004):1-19.
J.R. Cebral, F. Mut, J. Weir, C. Putman. Quantitative Characterization of the hemodynamic environment in ruptured and unruptured brain aneurysms. AJNR Am J Neuroradiol 32(2011):145-151.
Safaee M, Burke J, Mcdermott M W. Techniques for the Application of Stereotactic Head Frames Based on a 25-Year Experience. Cureus 8(3, 2016): e543. DOI 10.7759/cureus.543, pp. 1-15.
Nam K. Yoon, Scott McNally, Philipp Taussky and Min S. Park. Imaging of cerebral aneurysms: a clinical perspective. Neurovascular Imaging 2:6 (2016) DOI: 10.1186/s40809-016-0016-3, pp. 1-7.
Shepard DM, Ferris MC, Ove R, Ma L. Inverse treatment planning for Gamma Knife radiosurgery. Med Phys 27(12,2000):2748-2756.
Robert M. Starke, Nohra Chalouhi, Dale Ding, and David M. Hasan. Potential role of aspirin in the prevention of aneurysmal subarachnoid hemorrhage. Cerebrovasc Dis 39(0,2015):332-342.
Derek L G Hill, Philipp G Batchelor, Mark Holden and David J Hawkes. Medical image registration. Phys. Med. Biol. 46(2001):R1-R45.
J. B. Antoine Maintz and Max A. Viergever. An Overview of Medical Image Registration Methods. In: Proceedings of the 1996 Symposium of the Belgian hospital physicists association (SBPH-BVZP), vol. 12, pp. V:1-22. 1996.
Nisreen Sulayman, Moustafa Al-Mawaldi, Qosai Kanafani. Semiautomatic detection and segmentation algorithm of saccular aneurysms in 2D cerebral DSA images. The Egyptian Journal of Radiology and Nuclear Medicine 47(2016):859-865.
A. Sutou and Y. Dai. Global optimization approach to unequal sphere packing problems in 3D. Journal of Optimization Theory and Applications 114(3,2002):671-694.
Hamid R. Ghaffari. Optimization models and techniques for radiation treatment planning applied to Leksell Gamma Knife Perfexion. PhD Thesis. Department of Mechanical and Industrial Engineering. University of Toronto. 2012. pp. 1-116.
Meng H, Wang Z, Hoi Y, Gao L, Metaxa E, Swartz DD, Kolega J. Complex hemodynamics at the apex of an arterial bifurcation induces vascular remodeling resembling cerebral aneurysm initiation. Stroke 38(6,2007):1924-1931.
H. Meng, V.M. Tutino, J. Xiang, and A. Siddiqui. High WSS or Low WSS? Complex Interactions of Hemodynamics with Intracranial Aneurysm Initiation, Growth, and Rupture: Toward a Unifying Hypothesis. AJNR Am J Neuroradiol 35(2014):1254-1262.
Juhana Frosen, Riikka Tulamo, Anders Paetau, Elisa Laaksamo, Miikka Korja, Aki Laakso, Mika Niemela, and Juha Hernesniemi. Saccular intracranial aneurysm: pathology and mechanisms. Acta Neuropathol 123(6,2012):773-786.
Hopewell JW, Campling D, Calvo W, Reinhold HS, Wilkinson JH, Yeung TK. Vascular irradiation damage: its cellular basis and likely consequences. Br J Cancer Suppl. 7(1986):181-191.
Fajardo LF, Berthrong M. Vascular lesions following radiation. Pathol Annu. 23(Pt 1,1988):297-330.
Rodemann HP, Blaese MA. Responses of normal cells to ionizing radiation. Semin Radiat Oncol. 17(2,2007):81-88.
O'Connor MM, Mayberg MR. Effects of radiation on cerebral vasculature: a review. Neurosurgery 46(1,2000):138-149.
Halle M, Hall P, Tornvall P. Cardiovascular disease associated with radiotherapy: activation of nuclear factor kappa-B. J Intern Med. 269(5,2011):469-477.
Xu J, Cao Y. Radiation-induced carotid artery stenosis: a comprehensive review of the literature. Interv Neurol. 2(4,2014):183-192.
Muller DWM, Ellis SG, Topel EJ. Experimental models of coronary artery restenosis. J Am Coll Cardiol 1992; 19(1992): 418-432.
Ip JH, Fuster V, Badimon L, et al. Syndromes of accelerated atherosclerosis: role of vascular injury and smooth muscle proliferation. J Am Coll Cardiol 15(1990): 1667-1687.
Wilentz JR, Sanborn TA, Haundenschild CC, et al. Platelet accumulation in experimental angioplasty: time course and relation to vascular injury. Circulation 75(1987): 636-642.
Castellot JJ Jr, Addonizio ML, Rosenberg R, et al. Cultured endothelial cells produce a heparin-like inhibitor of smooth muscle growth. J Cell Biol 90(1981): 372-377.
Campbell GR, Campbell JH. Smooth muscle phenotypic changes in the arterial wall homeostasis: implications for the pathogenesis of atherosclerosis. Exp Mol Path 42(1985):139-162.
Forrester JS, Fishbein M, Helfant R, et al. A paradigm for restenosis based on cell biology: clues for the development of new preventative therapies. J Am Coll Cardiol 17(1991):758-769.
Schwartz RS, Holmes D Jr, Topol E. The restenosis paradigm revisited: an alternative proposal for cellular mechanisms. J Am Coll Cardiol 20(1992):1284-1293.
Clowes AW, Reidy MA, Clowes MM. Kinetics of cellular proliferation after arterial injury. I. Smooth muscle growth in the absence of endothelium. Lab Invest 49(1983): 327-333.
Bavinski G, Talazoglu V, Killer M, Richling B, Gruber A, Gross CE, Plenk H Jr. Gross and microscopic histopathological findings in aneurysms of the human brain treated with Guglielmi detachable coils. J Neurosurg 91(1999):284-293.
Raymond J, Venne D, Alias S, Roy D, Oliva VL, Denbow N, Salazkin I, Leclerc G. Healing mechanisms in experimental aneurysms, I: vascular smooth muscle cells and neointima formation. J Neuroradiol. 26(1999):7-20.
Raymond J, Guilbert F, Metcalfe a, Gévry G, Salazkin I, Robledo O. Role of the Endothelial Lining in Recurrences After Coil Embolization Prevention of Recanalization by Endothelial Denudation. Stroke 35(2004):1471-1475.
Ivanilson Alves de Oliveira. Main Models of Experimental Saccular Aneurysm in Animals, Chapter 3, pp. 43-64 In: Aneurysm, Dr. Yasuo Murai (Ed.), InTech, DOI: 10.5772/50310 (2012).
Press, WH, Teukolsky, SA, Vetterling, WT, Flannery, BP. Section 16.5. Support Vector Machines. In: Numerical Recipes: The Art of Scientific Computing (3rd ed.). New York: Cambridge University Press, 2007, pp. 883-898.
Christopher J.C. Burges. A tutorial on support vector machines for pattern recognition. Data Mining and Knowledge Discovery 2(1998):121-167.
J.A.K. Suykens, J. Vandewalle, B. De Moor. Optimal Control by Least Squares Support Vector Machines. Neural Networks 14 (2001):23-35.
Sapankevych, N.and Sankar, R. Time Series Prediction Using Support Vector Machines: A Survey. IEEE Computational Intelligence Magazine 4(2,2009):24-38.

(56) References Cited

OTHER PUBLICATIONS

Alex J. Smola and Bernhard Scholkopf. A tutorial on support vector regression. Journal of Statistics and Computing 14(3,2004):199-222.
Felipe Alonso-Atienza, José Luis Rojo-Álvarez, Alfredo Rosado-Muñoz, Juan J. Vinagre, Arcadi García-Alberola, Gustavo Camps-Valls. Feature selection using support vector machines and bootstrap methods for ventricular fibrillation detection. Expert Systems with Applications 39(2012): 1956-1967.
Anonymous. Definition of "beam". Downloaded on Jun. 21, 2019 from the web site https://www.tabers.com/tabersonline/view/Tabers-Dictionary/738619/all/beam?q=beam. Publisher: Taber's Medical Dictionary.
Anonymous. Leksell Gamma Knife (R) Treatment Statistics Report 1968-2016, slide No. 13., entitled Leksell Gamma Knife® Indications Treated 1968-2016, Worldwide. Downloaded from the web site https://slideplayer.com/slide/12895659/ on Apr. 22, 2019.
Anonymous. Leksell Gamma Knife (R) Treatment Statistics Report 1968-2016, slide No. 30., entitled Leksell Gamma Knife® Functional Disorders Treated Annually, Worldwide. Downloaded from the web site https://slideplayer.com/slide/12895659/ on Apr. 22, 2019.
Anonymous. Leksell Gamma Knife (R) Treatment Statistics Report 1968-2016, slide No. 46, entitled Leksell Gamma Knife® Vascular Disorders Treated Annually, Worldwide. Downloaded from the web site https://slideplayer.com/slide/12895659/ on Apr. 22, 2019.
Jason P. Sheehan, Brian D. Kavanagh, Anthony Asher and Robert E. Harbaugh. Inception of a national multidisciplinary registry for stereotactic radiosurgery. J Neurosurg. 124(1,2016):155-162.
Anonymous. Definition of "noninvasive". Downloaded on Jun. 19, 2016 from the web site https://medlineplus.gov/ency/article/002269.htm. Publisher: NIH MedlinePlus Medical Encyclopedia.
Anonymous. Definition of "integral". Downloaded on Jun. 24, 2019 from the web site https://dictionary.cambridge.org/us/dictionary/english/integral. Publisher: Cambridge Dictionary.
Anonymous. Definition of "integral". Downloaded on Jun. 24, 2019 from the web site https://www.dictionary.com/browse/integral. Publisher: dictionary.com.
Korja M, Kivisaari R, Rezai Jahromi B, Lehto H. Natural History of Ruptured but Untreated Intracranial Aneurysms. Stroke. 48(4, 2017):1081-1084.
Junjie Zhou, Hao Lin, Richard Summers, Mingmin Yang, Brian G. Cousins, and Janice Tsui. Current Treatment Strategies for Intracranial Aneurysms: An Overview. Angiology. 69(1, 2018): 17-30 on its p. 20, col. 2, last paragraph.
Muhammad Dzafir Ismail, Wan Azman Wan Ahmad, Matthias Leschke, et al. The outcomes of patients with very small coronary artery disease treated with thin strut cobalt chromium bare metal stents: an observational study. Springerplus. 2016; 5(1, 2016): 1668. pp. 1-9.
Anonymous. Definition of "adjacent". Downloaded on Jun. 21, 2019 from the web site https://en.oxforddictionaries.com/definition/adjacent. Publisher: Oxford Dictionary.
David Garrod, ed. Definition of "disposed". Glossary of Judicial Claim Constructions in the Mechanical, Electro-Mechanical and Medical Devices Arts, Compiled and edited by David Garrod. Public Patent Foundation, Inc. Benjamin N. Cardozo School of Law, 55 Fifth Avenue, New York, N.Y. 10003. p. 105.
Schillinger, M and E Minar. Advances in vascular brachytherapy over the last 10 years: focus on femoropopliteal applications. J Endovasc Ther.11 (Dec. 2004) Suppl 2:II180-191.
Liu Y, Flynn RT, Kim Y, Yang W, Wu X. Dynamic rotating-shield brachytherapy. Med Phys. 40 (Dec. 12, 2013):121703, pp. 1-11.
Anonymous. Description of electron beam therapy. Downloaded on Jun. 21, 2016 from the web site https://radiopaedia.org/articles/electron-therapy?lang=us. Publisher: Radiopaedia.
Wang Y, Pantelias GE, Iliakis G. Mechanism of radiosensitization by halogenated pyrimidines: the contribution of excess DNA and chromosome damage in BrdU radiosensitization may be minimal in plateau-phase cells. Int J Radiat Biol 66(2,1994):133-142.

Alexander Keedy. An overview of intracranial aneurysms. Mcgill J Med. 9(2,2006): 141-146, on p. 143, col. 1, 2nd paragraph.
Anonymous. Definition of "aneurysmal sac". Downloaded on Jun. 21, 2019 from the web site https://medical-dictionary.thefreedictionary.com/aneurysmal+sac. Publisher: dictionary.com.
Anonymous. Definition of "functional neurological disorder". Downloaded on Jun. 11, 2019 from the web site https://rarediseases.org/rare-diseases/fnd/. Publisher: National Organization of Rare Diseases.
Anonymous. Definition of "functional neurosurgery". Downloaded on Jun. 21, 2019 from the web site https://medical-dictionary.thefreedictionary.com/functional+neurosurgery. Publisher: The Free Dictionary—Medical Dictionary.
Anonymous. Definition of "instantiate". Downloaded on Jun. 26, 2019 from the web site https://www.merriam-webster.com/dictionary/instantiate. Publisher: Merriam-Webster.
Anonymous. Definition of "instantiate". Downloaded on Jun. 26, 2019 from the web site https://en.wiktionary.org/wiki/instantiate. Publisher: Wiktionary.
John Macleod. Definition of "instantiate". Downloaded on Jun. 26, 2019 from the web site https://whatis.techtarget.com/definition/instantiation. Publisher: TechTarget.
Gupta V, Chugh M, Jha AN, Walia BS, Vaishya S. Coil embolization of very small (2 mm or smaller) berry aneurysms: feasibility and technical issues. AJNR Am J Neuroradiol 30(2,2009):308-314.
Khalid M. Abbed KM and Christopher S Ogilvy. Intracerebral hematoma from aneurysm rupture. Neurosurg Focus. 15(4, Oct. 15, 2003): Article 4, pp. 1-4.
Alyson R. Zazulia, MD; Michael N. Diringer, MD; Colin P. Derdeyn, MD; William J. Powers, MD. Progression of Mass Effect After Intracerebral Hemorrhage. Stroke 30 (1999):1167-1173.
Beth Rush. Mass Effect. In: Kreutzer J.S., DeLuca J., Caplan B. (eds) Encyclopedia of Clinical Neuropsychology. Springer, New York, NY (2011), p. 112.
Cornelissen BM, Schneiders JJ, Potters WV, van den Berg R, Velthuis BK, Rinkel GJ, Slump CH, Van Bavel E, Majoie CB, Marquering HA. Hemodynamic Differences in Intracranial Aneurysms before and after Rupture. AJNR Am J Neuroradiol. 36(Oct. 10, 2015):1927-1933, See: p. 1929, col. 2, para. 2.
Schneiders JJ, Marquering HA, van den Berg R, Van Bavel E, Velthuis B, Rinkel GJ, Majoie CB. Rupture-associated changes of cerebral aneurysm geometry: high-resolution 3D imaging before and after rupture. AJNR Am J Neuroradiol. 35(Jul. 7, 2014):1358-1362, See: Fig. 3 on p. 1362.
P. Ashley Wackym, Christina L. Runge-Samuelson, David R. Friedland. Stereotactic Radiosurgery of Skull Base Tumors. Chapter 26 In: Otologic Surgery (Third Edition) 2010, pp. 785-798 (Saunders/Elsevier Publ., Philadelphia PA).
David M. Shepard, Cedric Yu, Martin Murphy, Marc R. Bussiere and Frank J Bova. Treatment Planning for Sterotactic Radiosurgery. pp. 69-90 in: Principles and Practice of Stereotactic Radiosurgery edited by Lawrence S. Chin, William F. Regine. Springer, NY (2008), See: pp. 76-78.
Joseph Michael Bowling. Leksell Gamma Knife Treatment Planning via Kernel Regression Data Mining Initialization and Genetic Algorithm Optimization. PhD dissertation, University of Tennessee, 2012, pp. 1-411, See: pp. 73-75 and software code in its Appendix.
Dave Brolley, William Cohen, Roland Grunberg, et. al. Red Hat Enterprise Linux 6 Developer Guide. Red Hat, Inc. 1801 Varsity Drive, Raleigh, NC 27606-2072 USA (2010), See: pp. 5-19.
Anonymous. "Variables and Memory Addresses" at the web site http://icarus.cs.weber.edu/~dab/cs1410/textbook/4.Pointers/vars_address.html downloaded from the internet on Nov. 3, 2019.
Anonymous. "Memory Layout of C Programs" at the web site https://www.geeksforgeeks.org/memory-layout-of-c-program/ downloaded from the internet on Nov. 3, 2019.
A. Sam Beddar, Peter J. Biggs, Gary A. Ezzell. et. al. Intraoperative radiation therapy using mobile electron linear accelerators: Report of AAPM Radiation Therapy Committee Task Group No. 72. Med. Phys. 33(May 5, 2006): 1476-1489. See Figs. 7 and 8.
Schwartz RS, Koval TM, Edwards WD, et al. Effect of external beam irradiation on neointimal hyperplasia after experimental coronary artery injury. J Am Coll Cardiol 1992:19:1106-1113.

(56) References Cited

OTHER PUBLICATIONS

Schwartz RS et al. Restenosis after balloon angioplasty. A practical proliferative model in porcine coronary arteries. Circulation. 82 (Dec. 6, 1990):2190-2200.
Anonymous. X-Ray Unit has Wide Range. Popular Science Monthly 156 (Mar. 1950): 164.

* cited by examiner

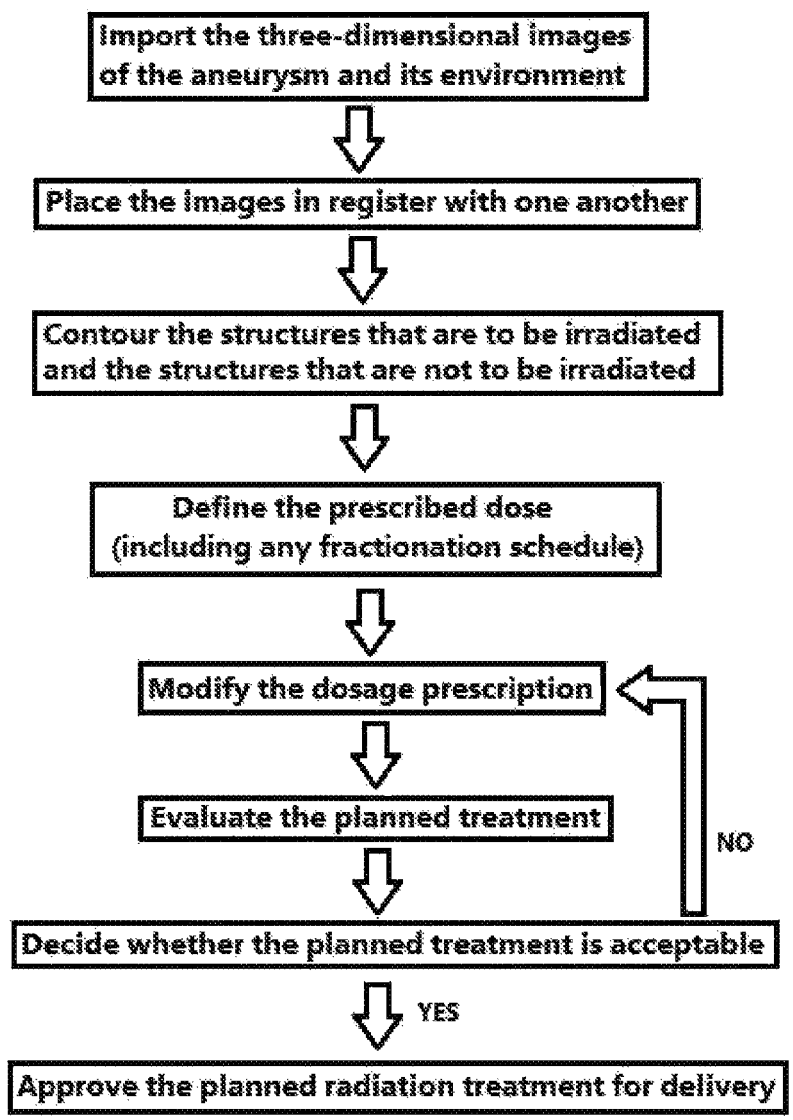

H = dome height
D = dome diameter
N = neck width
S = dome semi-axis height

TREATMENT OF UNRUPTURED SACCULAR INTRACRANIAL ANEURYSMS USING STEREOTACTIC RADIOSURGERY

BACKGROUND OF THE INVENTION

The field of the present invention is the treatment of intracranial aneurysms using focused ionizing radiation. An intracranial aneurysm (brain aneurysm) is a disorder in which weakness in the wall of a cerebral artery causes a localized dilation or ballooning of the blood vessel. Intracranial aneurysms are classified into several basic types—the rounded saccular aneurysms; the spindle-shaped fusiform aneurysms; and Charcot-Bouchard aneurysms (also known as microaneurysms or miliary aneurysms). Charcot-Bouchard aneurysms are associated with hypertension and occur in blood vessels less than 300 microns in diameter, particularly in the lenticulostriate vessels of the basal ganglia. Blister-like aneurysms, traumatic and dissecting aneurysms, and infectious aneurysms have also been described. For each of these aneurysm types, all layers of the blood vessel wall are dilated or ballooned, such that a portion of the blood vessel lumen itself is enlarged. In contrast to those true aneurysms, the wall of an intracranial pseudoaneurysm (false aneurysm) is composed mainly of blood clot and fibrous tissue that does not distend all layers of the blood vessel, because it forms only between internal layers of a vessel wall.

The present invention is concerned in particular with the treatment of saccular aneurysms, which are rounded, berry-like outpouchings that arise primarily from arterial bifurcation points. In contrast to fusiform aneurysms that are generally associated with atherosclerosis and that are found in portions of arteries in locations upstream of major bifurcations or branch points, saccular aneurysms are found at the apex of bifurcations at the origin of small arteries branching from large ones, and on the sidewall of arteries with sharp curvatures. Saccular aneurysms account for approximately 90% of intracranial aneurysms and mainly appear in the intracranial arteries about and near the Circle of Willis, which is a circulatory anastomosis that supplies blood to the brain. The Circle of Willis comprises the anterior communicating artery and the following left and right arteries: anterior cerebral artery, internal carotid artery, posterior cerebral artery and posterior communicating artery. Over 85% of the brain aneurysms form in the anterior part of the circle, which is supplied by the two carotid arteries.

When an aneurysm ruptures, blood flows from the aneurysm lumen into the subarachnoid space, which is the opening between the arachnoid membrane and the pia mater surrounding the brain. The result is a form of stroke known as a subarachnoid hemorrhage. Symptoms of a subarachnoid hemorrhage include a severe headache with a rapid onset ("thunderclap headache"), vomiting, confusion or a lowered level of consciousness, and sometimes seizures. The association of meningeal signs should also raise suspicion of a subarachnoid hemorrhage [VAN GUN J, Kerr R S, Rinkel G J. Subarachnoid haemorrhage. Lancet 369 (9558, 2007): 306-318]. Some ruptured aneurysms are also accompanied by a hematoma, i.e., a localized swelling that is filled with leaked blood that is usually clotted or partially clotted [Khalid M. ABBED K M and Christopher S Ogilvy. Intracerebral hematoma from aneurysm rupture. Neurosurg Focus. 15(4, Oct. 15, 2003): Article 4, pp. 1-4]. Hematomas can exert a clinically significant mass effect, where "mass effect" refers to the distortion, displacement and/or compression of areas of brain tissue that surround space that is newly-occupied by the leaked blood [Allyson R. ZAZULIA, MD; Michael N. Diringer, MD; Colin P. Derdeyn, MD; William J. Powers, MD. Progression of Mass Effect After Intracerebral Hemorrhage. Stroke 30 (1999):1167-1173; Beth RUSH. Mass Effect. In: Kreutzer J. S., DeLuca J., Caplan B. (eds) Encyclopedia of Clinical Neuropsychology. Springer, New York, N.Y. (2011), page 112]. Following the rupture of a cerebral aneurysm, a perianeurysmal hematoma can exert a mass effect on the ruptured aneurysm itself, by pressing on the aneurysm to change its shape and by displacing the aneurysm from its original location, an example of which is the observed displacement of an aneurysm by 8.9 mm after rupture, due to the formation of a perianeurysmal hematoma having dimensions 28×22×35 mm [CORNELISSEN B M, Schneiders J J, Potters W V, van den Berg R, Velthuis B K, Rinkel G J, Slump C H, Van Bavel E, Majoie C B, Marquering H A. Hemodynamic Differences in Intracranial Aneurysms before and after Rupture. AJNR Am J Neuroradiol. 36(10, October 2015):1927-1933, on p. 1929; SCHNEIDERS J J, Marquering H A, van den Berg R, Van Bavel E, Velthuis B, Rinkel G J, Majoie C B. Rupture-associated changes of cerebral aneurysm geometry: high-resolution 3D imaging before and after rupture. AJNR Am J Neuroradiol. 35(7, July 2014):1358-1362, see its FIG. 3].

Most aneurysms do not cause symptoms until they rupture. When they do rupture, they are associated with significant morbidity and mortality. The most common presentation of an intracranial aneurysm is, in fact, a subarachnoid hemorrhage. In North America, 80-90% of non-traumatic subarachnoid hemorrhages are caused by rupture of an intracranial aneurysm. Of patients with a subarachnoid hemorrhage, 10-15% promptly die, 50% die within a month, and 50% of survivors have neurological deficits. Ruptured aneurysms have their highest rebleeding rate within the first day. If untreated, at least 50% rebleed during the 6 months after the initial hemorrhage. Immediate care along with aggressive anti-ischemic treatment, such as antivasospastic drugs, intravascular volume expansion and transcranial doppler monitoring, are often crucial to achieving the best possible outcome.

An aneurysm may be detected incidentally during the diagnosis or treatment of some other brain disorder. But most times the patient's aneurysm is latent until it causes symptoms. Therefore, for some patients it may be advisable to screen for aneurysms. The patients at highest risk are those for whom aneurysms run in their families, patients exhibiting multiple- or previously ruptured aneurysms, and patients exhibiting certain conditions such as systemic lupus erythematosus and genetic disorders such as autosomal dominant polycystic kidney disease [Hae Woong JEONG, Jung Hwa Seo, Sung Tae Kim, Cheol Kyu Jung, and Sang-il Suh. Clinical practice guideline for the management of intracranial aneurysms. Neurointervention 9(2014):63-71].

According to angiography and autopsy studies, the prevalence of intracranial aneurysms ranges from 0.5%-6% in adults. The risk of aneurysm rupture is difficult to determine precisely, but is estimated to be cumulatively 1-2% per year, for asymptomatic lesions that have not yet ruptured. With a combined operative mortality rate and major morbidity risk of about 3.5% for aneurysm surgery performed by a skilled physician, imprecise conclusions are that any patient with a life expectancy of more than 3 years would benefit from surgical obliteration of an unruptured asymptomatic aneurysm. Ruptured aneurysms that are not treated have a very high risk of rebleeding after the initial hemorrhage has occurred. The risk is estimated at 20-50% in the first 2 weeks, and such rebleeding carries a mortality rate of nearly 85%.

Depending on the aneurysm's location, more precise individualized treatment algorithms indicate that unruptured aneurysms should be treated surgically if they exceed a certain diameter and/or expansion growth rate and/or aspect ratio (aneurysm depth to aneurysm neck) [NADER-SEPAHI A, Casimiro M, Sen J, Kitchen N D. Is aspect ratio a reliable predictor for intracranial aneurysm rupture? Neurosurgery 54 (6, 2004): 1343-1348; UJIIE H, Tachibana H, Hiramatsu O, Hazel A L, Matsumoto T, et al. Effects of size and shape (aspect ratio) on the hemodynamics of saccular aneurysms: a possible index for surgical treatment of intracranial aneurysms. Neurosurgery 45 (1, 1999): 119-130]. This leaves physicians with the therapeutic dilemma of either subjecting patients with borderline smaller aneurysms to a complex surgery having high morbidity and complications, or simply surveilling an aneurysm having a risk of rupture that might be acceptable. It is worth noting that 13% of ruptured aneurysms are less than 5 mm in diameter, so aneurysm size alone should not be the only consideration [KASSELL N F, Torner J C. Size of intracranial aneurysms. Neurosurgery 12(1983):291-297].

Accordingly, grading scales have been developed to help decide objectively the likelihood that a patient with an aneurysm will not experience a rupture, or to suggest the most appropriate time to perform surgery if a rupture has already occurred. The most commonly used grading scales are the Hunt and Hess Scale, the Fisher Scale, the Glasgow Coma Score, and the World Federation of Neurological Surgeons (WFNS) Scale. But no less than 40 other scales have been proposed. The Hunt and Hess Scale and the modified Fisher Scale both assign grade 0 to an unruptured aneurysm and therefore do not contemplate heterogeneous risks among unruptured aneurysms. In contrast, some scales are designed specifically for unruptured aneurysms [HUNT W E, Hess R M. Surgical risk as related to time of intervention in the repair of intracranial aneurysms. J Neurosurg 28(1968):14-20; FRONTERA J A, Claassen J, Schmidt J M, Wartenberg K E, Temes R, Connolly E S Jr, MacDonald R L, Mayer S A. Prediction of symptomatic vasospasm after subarachnoid hemorrhage: the modified fisher scale. Neurosurgery 59 (1, 2006): 21-27; OGILVY, Christopher S. and Carter, Bob S. A Proposed Comprehensive Grading System to Predict Outcome for Surgical Management of Intracranial Aneurysms. Neurosurgery 42 (5, 1998): 959-968; KHANNA R K, Malik G M, Qureshi N: Predicting outcome following surgical treatment of unruptured intracranial aneurysms: A proposed grading system. J Neurosurg 84(1996): 49-54].

Instead of, or in addition to, the use of grading scores, other authorities provide somewhat more subjective advice about the treatment of unruptured and ruptured aneurysms, which is intended to shape the judgment of the physician who will either treat or surveil the aneurysm [SOLOMON R A, Fink M E, Pile-Spellman J: Surgical management of unruptured intracranial aneurysms. J Neurosurg 80(1994): 440-446; SONOBE M, Yamazaki T, Yonekura M, Kikuchi H. Small unruptured intracranial aneurysm verification study: SUAVe study, Japan. Stroke 41(2010):1969-1977].

Surgical ligation and clipping has been the standard treatment of intracranial aneurysms for decades. Microsurgical techniques have evolved over the years, and a variety of surgical approaches and metal aneurysm clips have been developed. For patients having complex aneurysms, bypass surgery and vascular reconstruction may be needed. Surgical treatment has proven to be highly effective, with reported rates of complete occlusion of unruptured aneurysms of approximately 90-95%, with an extremely low rate of subsequent subarachnoid hemorrhage. Surgical repair of aneurysms in the posterior intracranial circulation, however, is extremely difficult due to technical access issues [POLEVAYA N V, Kalani M Y, Steinberg G K, Tse V C. The transition from hunterian ligation to intracranial aneurysm clips: a historical perspective. Neurosurg Focus 20 (6, 2006):E3, pp. 1-7; Nicola ACCIARRI, Giovanni Toniato, Andreas Raabe, and Giuseppe Lanzion. Clipping techniques in cerebral aneurysm surgery. Journal of Neurological Sciences 60 (1, 2016): 83-94; Harley Brito D A SILVA, Mario Messina-Lopez, and Laligam N. Sekhar. Bypasses and Reconstruction for Complex Brain Aneurysms. Methodist Debakey Cardiovasc J. 10 (4, 2014): 224-233].

In 1991, Guido Guglielmi described a technique of occluding aneurysms with an endovascular approach using an electrolytic detachable platinum coil [U.S. RE42756, to GUGLIELMI et al, entitled Endovascular electrolytically detachable wire and tip for the formation of thrombus in arteries, veins, aneurysms, vascular malformations and arteriovenous fistulas]. In this procedure, one or more coils are introduced under radiologic guidance directly into the aneurysm via a microcatheter. The first coil is introduced into the aneurysm dome to form a basket, with subsequent coils of decreasing size placed within the aneurysm. The coils fill the aneurysm, blocking blood flow. A low positive direct electric current is then delivered to the guide wire. Thrombosis occurs within the aneurysm due to the attraction of negatively charged white blood cells, red blood cells, platelets and fibrinogen to the positively charged platinum coil within the aneurysm. Electrical current detaches the platinum coil within a few minutes due to electrolysis of the stainless steel wire closest to the thrombus-covered coil. The coiling may also be performed in conjunction with the use of a stent or balloon. For example, a wide-neck saccular aneurysm has a neck width of at least 4 mm, or a neck at least twice as wide as the height of the aneurysm dome, and it may be difficult for the coils to remain in such an aneurysm without the use of a stent. Recanalization of an aneurysm occurs when a previously treated aneurysm refills with blood. Recent studies indicate that recanalization occurs in more than 20% of coiled unruptured aneurysms and in more than 40% of coiled ruptured aneurysms. Consequently, many of these patients require re-coiling or open clip ligation [Brad SEIBERT, Ramachandra P. Tummala, Ricky Chow, Alireza Faridar, Seyed A. Mousavi and Afshin A. Divani. Intracranial aneurysms: review of current treatment options and outcomes. Frontiers in Neurology 2 (45, July 2011), doi: 10.3389/fneur.2011.00045, pp. 1-11; I. Y. L. TAN, R. F. Agid, and R. A. Willinsky. Recanalization rates after endovascular coil embolization in a cohort of matched ruptured and unruptured cerebral aneurysms. Interv Neuroradiol. 17 (1, 2011): 27-35].

More recently, the treatment of aneurysms has also been performed using stent devices that promote aneurysm thrombosis by diversion of flow through the parent vessel's lumen. The rationale of flow diversion is to treat the diseased vessel segment near the aneurysm, instead of directly treating the aneurysm itself. The parent artery adapts to the disruption of blood flow, leading to natural thrombosis by stasis within an aneurysm. The thrombosis is later reabsorbed while the artery is sealed in the presence of the flow diversion device. Sometimes, however, instead of remodeling the parent vessels and aneurysms, thrombus-associated autolysis of the aneurysm wall may also result in delayed rupture. Flow diversion devices are currently approved for treating unruptured large and giant aneurysms from the internal carotid artery between the superior hypophyseal and cavernous segments. Even so, it is thought that flow diversion can also be used in treating ruptured aneurysms, posterior circulation aneurysms, and distal anterior circulation aneurysms [Pietro I. D'URSO, Giuseppe Lanzino, Harry J. Cloft and David F. Kallmes. Flow Diversion for Intracranial Aneurysms: A Review. Stroke 42(2011):2363-2368; Adam M. BROUILLARD, Xingwen Sun, Adnan H. Siddiqui, Ning Lin. The use of flow diversion for the treatment of intracranial aneurysms: expansion of indications. Cureus 8(1): e472. DOI 10.7759/cureus.472. pp. 1-8; KULCSAR Z, Houdart E, Bonafé A et al. Intra-aneurysmal thrombosis as a possible cause of delayed aneurysm rupture after flow-diversion treatment. AJNR Am J Neuroradiol. 32 (1, 2011): 20-25].

Aneurysms that are associated with arteriovenous malformations (AVMs) are special in that they might be treated by stereotactic radiosurgery (SRS), incidental to radiological treatment of the AVM itself. An AVM is a tangle of blood vessels in the brain, or on the brain's surface, that bypasses normal brain tissue and diverts blood directly from the arteries to the veins without the presence of a capillary bed. AVMs can occur anywhere within the brain, are relatively uncommon (<1% of the population, more commonly in males than females) and are usually congenital. Aneurysms are associated with AVMs in approximately 8.5% of patients with AVMs [Michael T. LAWTON, W. Caleb Rutledge, Helen Kim, et al. Brain arteriovenous malformations. Nature Reviews Disease Primers 1, Article number: 15008 (2015) doi:10.1038/nrdp.2015.8, pp. 1-20; Esther J. KIM, Sandra Vermeulen, Francisco J. Li, David W. Newell. A review of cerebral arteriovenous malformations and treatment with stereotactic radiosurgery. Transl Cancer Res 3 (4, 2014): 399-410]. If the AVM is not too large and is in a location of the brain that is difficult to reach by conventional surgery, its treatment with SRS may be indicated. In this procedure, angiography, computed tomography, and/or magnetic resonance imaging is first performed to localize the AVM. Then, stereotaxis is used to focus ionizing radiation from collimated beams onto the AVM to produce direct damage to its vessels. Traditionally, the stereotactic procedure uses a set of three coordinates and a mechanical device with head-holding clamps and bars, in order to put the patient's head in a fixed position in reference to the coordinate system. The objective is to point the beam(s) of radiation precisely inside the brain, at calculated coordinates for the AVM. The underlying mechanism of action for radiosurgery is thought to be the induction of neointimal thickening of the abnormal vasculature, which leads to progressive narrowing and eventual vessel occlusion [CHANG S D, Shuster D L, Steinberg G K, Levy R P, Frankel K: Stereotactic radiosurgery of arteriovenous malformations: Pathologic changes in resected tissue. Clin Neuropathol 16(1997):111-116].

Three types of radiosurgical devices have been used for SRS—the Gamma Knife stereotactic radiosurgery apparatus (Elekta, Sweden); Linear Accelerator (LINAC) devices such as the CYBERKNIFE® (Accuray, Sunnyvale, Calif.), NOVALIS Tx™ (BrainLab, Germany), XKNIFE™ (Integra, New Jersey), and AXESSE™ (Elekta, Sweden) stereotactic radiosurgery apparatus, (among others); and proton beam devices. The Gamma Knife stereotactic radiosurgery apparatus uses multiple, simultaneous beams of gamma rays (from the radioactive decay of Cobalt-60) that converge at a fixed point after the patient has been positioned using a special couch, namely, the point in the patient's brain that is being treated. The original Gamma Knife devices used hemispherically arranged beams. The LINAC devices use a single X-ray beam that is produced by accelerating electrons onto a metal target. The X-ray beam is directed towards the patient from multiple sequential directions, so the underlying principle is the same as that of the Gamma Knife devices, except that the beams are applied sequentially rather than simultaneously. The term "beam" is defined here, as in Taber's medical dictionary, to be "Photons, atomic particles, or sound waves aligned in parallel rays." According to this definition, a single photon or atomic particle cannot constitute a "beam" because the term refers to the substantially parallel alignment of multiple rays with respect one another. Also, a point source that emits photons or atomic particles in all directions cannot produce a beam of radiation (because omnidirectional rays are inherently not parallel with one another), unless the point source is accompanied by a waveguide or collimation-aperture device that minimizes ray divergence or eliminates rays of radiation that are not aligned substantially parallel to one another. A stereotactic head frame may also be used with the LINAC device, but newer techniques use robotics (e.g., industrial robotic arm used in the CYBERKNIFE® stereotactic radiosurgery apparatus) in which real-time imaging is performed to track the location of the target tissue as treatment is performed, thereby eliminating the need for a stereotactic head frame. The term "stereotactic radiosurgery" is used herein to include the use of methods for which a stereotactic head frame is not needed, because the targeting method is still based on stereotaxy. In addition to stereotactic radiosurgical devices that use gamma or X-rays, there also exist devices that irradiate the patient with charged particles (ordinarily protons, but could also be 1H, 4He, 12C, or 16O) [Timothy D. SOLBERG, Robert L. Siddon, and Brian Kavanagh. Historical Development of Stereotactic Ablative Radiotherapy. pp. 9-35 In: S. S. Lo et al. (eds.), Stereotactic Body Radiation Therapy, Medical Radiology. Berlin and Heidelberg: Springer-Verlag, 2012].

For the less than 10% of AVMs that have an associated aneurysm, stereotactic radiosurgery should not be considered to be a treatment of the aneurysm per se. This is because the whole AVM is irradiated, preferably with doses of 16 to 25 Gy at the margins of the AVM, with a sharp dose fall-off outside the treatment volume. According to LUNSFORD and his colleagues, if an aneurysm is located within the central part of the AVM (within the nidus, or location of the vessel tangle), the objective is to assure that the procedure does not cause a hemorrhage, rather than specifically to obliterate the aneurysm. If the aneurysm is located immediately proximal to the AVM (in the sense of blood flowing by the aneurysm and into the AVM), LUNSFORD says that the aneurysm will likely close as the AVM is obliterated, although that is not the primary objective of the stereotactic radiosurgery. However, if the aneurysm is located more than one arterial branch division proximal to the AVM, the aneurysm should be treated by itself, either before or immediately after the AVM stereotactic radiosurgery, using clipping or endovascular embolization [L. Dade LUNSFORD, Ajay Niranjan, Douglas Kondziolka, Sait Sirin and J. C. Flickinger. Arteriovenous Malformation Radiosurgery: A Twenty Year Perspective. Clinical Neurosurgery 55(2008): 108-119].

The present invention discloses that the treatment of an unruptured aneurysm that is not associated with an arteriovenous malformation can also be performed using a focused beam of ionizing radiation that is delivered to the brain of a patient, i.e., using SRS. The inventor is unaware of stereotactic radiosurgery having ever been used to treat a non-AVM-associated, unruptured aneurysm, even though stereotactic radiosurgery of the brain has been practiced routinely for over 50 years. In fact, as described below, it appears that there have been only two reported instances in which stereotactic radiosurgery might have been used successfully to treat even a ruptured, non-AVM-associated aneurysm, 15 cases in which such patients died shortly after SRS treatment of their ruptured aneurysm, and one case in which the outcome is unknown.

According to NIRANJAN and colleagues, a 61 year old woman had sustained a hemorrhage from an aneurysm. One of the early pioneers of stereotactic radiosurgery (Leskell) "insisted to try" stereotactic radiosurgery on her aneurysm. That stereotactic radiosurgery was evidently against the advice of his colleagues, otherwise NIRANJAN would not have used the term "insisted." Perhaps Leskell wanted to try using SRS because the patient is said to have refused conventional surgery to deal with the hemorrhaged aneurysm. The treatment apparently occurred before 1983, because in a historical account dated 1983, Leskell's group had already tried to treat five cases of arterial aneurysm (see below the work of Forster). Leskell did not publish details of the case anywhere, but angiograms documenting the woman's aneurysm appear in a 1985 book chapter by STEINER on the subject of treating AVMs, within a discussion of the mechanism of radiosurgical treatment of AVMs. STEINER notes that the woman had a "spasm of [the] posterior communicating and posterior cerebral arteries" and "was stuporous for several weeks following the ischemic effects of vasospasm following a subarachnoid hemorrhage." Because the spasm may have been considered by Leskell to be a risk factor for having another hemorrhage, that may have been another reason that Leskell decided to go ahead and treat the patient using SRS, rather than simply surveil the woman. At the time of the stereotactic radiosurgery, STEINER says that the spasm was not present, but clearly there was no guarantee that it would not return. In any event, after the stereotactic radiosurgery, the woman's aneurysm became progressively smaller over next 11 months, and it was eventually obliterated [A. NIRANJAN, L. D. Lunsford, J. C. Flickinger, J. Novotny, J. Bhatnager, and D. Kondziolka. Gamma Knife: Clinical Experience. Chapter 66 in: Textbook of Stereotactic and Functional Neurosurgery, Volume 1 (Andres M. Llano, Philip L. Gildenberg, and Ronald R. Tasker, eds.) Berlin: Springer, 2009. p. 1071; STEINER, L. Radiosurgery in cerebral arteriovenous malformations. In: Fein J M and Flamm E, editors. Cerebrovascular surgery, vol 4. New York: Springer-Verlag; 1985. pp. 1161-1215, at pp. 1209-1210; Lars LEKSELL. Stereotactic radiosurgery. Journal of Neurology, Neurosurgery, and Psychiatry 46(1983):797-803].

The woman's aneurysms had several unusual features that are apparent from her angiograms. First, the aneurysm was not located at the apex of a bifurcation where two small arteries branch from a larger one. Instead, it seems to be associated primarily with a single vessel. Second, as noted by NIRANJAN, "the posterior communicating artery adjacent to the aneurysm also progressively narrowed in caliber and ultimately was obliterated without a neurological deficit. The patient refused a vertebral angiography, so we cannot know whether the aneurysm would fill or not from posterior circulation." Therefore, the obliteration of the aneurysm after 11 months may just has well be attributable to the disappearance of the vessel to which it was attached, rather than to radiation that was administered solely to the aneurysm. The disappearance of the whole vessel leads one to suspect that it was experiencing vasculitis, which would also account for a weakening of the vessel wall that could give rise to the aneurysm in the first place. This is in contrast to the etiology of most saccular aneurysms, which involves characteristic blood flow patterns in the vicinity of vessel bifurcations, in combination with maladaptive remodeling of the vessel wall in response to the resulting localized hemodynamic stresses. Although all aneurysms may exhibit inflammation to some extent, in an ordinary saccular aneurysm, one would not expect the inflammation to be so pronounced that it would be accompanied by a vanishing vessel that is apparently experiencing vasculitis. Another explanation for the disappearance of the vessel might be that there was excessive unintentional irradiation of the vessel itself, and the resulting damage to the vessel ultimately brought about its resorption, secondarily obliterating the aneurysm.

STEINER commented that "It needs to be emphasized that radiosurgery is an inadequate treatment for aneurysms that have recently bled, and it remains to be determined whether it has any place in the treatment of aneurysms that have not bled." Evidently, Leskell's colleagues were at least willing to try stereotactic radiosurgery on more aneurysms that did not involve an AVM, and according to NIRANJAN, "an additional 15 cases of arterial aneurysms were treated by Forster at [the] Karolinska Institute. All except one died of a hemorrhage a few weeks to months after the Gamma Knife treatment." Apparently, those additional 15 cases were never described in any publication, presumably because Forster was not inclined to publish negative results. So, we have no way of knowing anything specific about the 15 cases, or what was different about the one patient who did not die soon after treatment. We can only infer that the negative experience concerning the radiosurgical treatment of ruptured aneurysms was communicated by word-of-mouth among all the practitioners of stereotactic radiosurgery at that time, who as of 1985 were developing stereotactic radiosurgery at only a very small number of sites around the world, primarily in Sweden [Lars LEKSELL. Stereotactic radiosurgery. Journal of Neurology, Neurosurgery, and Psychiatry 46(1983):797-803; Timothy D. SOLBERG, Robert L. Siddon, and Brian Kavanagh. Historical Development of Stereotactic Ablative Radiotherapy. pp. 9-35 In: S. S. Lo et al. (eds.), Stereotactic Body Radiation Therapy, Medical Radiology. Berlin and Heidelberg: Springer-Verlag, 2012].

The only other report of stereotactic radiosurgery being used to treat an aneurysm not associated with an AVM is also one in which a hemorrhage had already occurred. The aneurysm was not a saccular aneurysm, but was instead a Charcot-Bouchard aneurysm, i.e., one associated with a distal lenticulostriate artery. Again in this case, the patient had refused surgery to deal with the hemorrhaged aneurysm, so as a last resort, the physicians tried stereotactic radiosurgical treatment with a Gamma Knife. The patient recovered, and after 22 months, the aneurysm was found to have been obliterated. In their report of the case, the radiosurgeons state that the "excellent recovery is probably not the direct effect of the GKS [Gamma Knife Surgery] treatment because the treatment was done to prevent bleeding. How the patient recovered from the initial bleeding is still somewhat unknown and is a separate issue. From a single case, it is impossible to determine if GKS made the aneurysm disappear or if it resolved spontaneously. In other words, this is an anecdotal case so it cannot imply that there is necessarily cause and effect here" [LAN Z, Li J, You C, Chen J. Successful use of Gamma Knife surgery in a distal lenticulostriate artery aneurysm intervention. Br J Neurosurg 26 (1, 2012): 89-90]. Occasionally, aneurysms do in fact thrombose and obliterate spontaneously, and LAN's reservations concerning cause and effect applies not only to that case, but also to the above-mentioned case of the 61 year old woman [CHOI C-Y, Han S-R, Yee G-T, Lee C-H. Spontaneous regression of an unruptured and non-giant intracranial aneurysm. Journal of Korean Neurosurgical Society. 52 (3, 2012): 243-245; JAYAKUMAR P N, Ravishankar S, Balasubramaya K S, Chavan R, Goyal G. Disappearing saccular intracranial aneurysms: do they really disappear? Interventional Neuroradiology 13 (3, 2007): 247-254].

The present invention discloses that stereotactic radiosurgery can be used to treat unruptured saccular aneurysms that are not associated with an AVM. Despite the undisputed need for the treatment of at least some unruptured saccular aneurysms that are not associated with an AVM, nobody has ever reported having tried using stereotactic radiosurgery on such an aneurysm, even though the stereotactic radiosurgery of brain structures has become routine over the last 50 years. This is possibly due to the early negative experience involving 15 patients that was recounted above with regard to the radiosurgical treatment of ruptured aneurysms, as well as to the equivocal and anecdotal success that was reported in only two cases of ruptured aneurysms the 61 year old woman and the patient with an aneurysm associated with a lenticulostriate artery. The only other instance in which ionizing radiation has been used to treat an aneurysm involved brachytherapy with 32P (not gamma or X irradiation), in animal experiments that showed recanalization of thrombus after coil occlusion in experimental models can be inhibited by in situ beta radiation using 32P ion-implanted platinum coils [RAYMOND J, Mounayer C, Salazkin I, Metcalfe A, Gevry G, Janicki C, Roorda S, Leblanc P. Safety and effectiveness of radioactive coil embolization of aneurysms: effects of radiation on recanalization, clot organization, neointima formation, and surrounding nerves in experimental models. Stroke 37(8, 2006):2147-2152]. The present invention is fundamentally different from that 32P brachytherapy, because the work of RAYMOND and colleagues involved endovascular entry, whereas the present invention is noninvasive. According to the present disclosure and Taber's Medical Dictionary, noninvasive procedures are defined as follows. "Noninvasive procedures do not involve tools that break the skin or physically enter the body." And because more than 50% of the beta particles emitted by 32P are absorbed within 1 mm of tissue, use of 32P is generally incapable of reaching all sites in the vessel wall, unlike the present invention, which can also selectively target particular portions of the aneurysm (e.g., only the aneurysm dome).

A motivation for the present disclosure is that the decision as to whether to treat the aneurysm with clipping or coiling or flow diversion, versus surveillance of the aneurysm, is based in part on the estimated risk of the surgery involving clipping or coiling or flow diversion. The complication rate related to treating small unruptured aneurysms using open surgery is reportedly approximately 4%. Because stereotactic radiosurgery avoids the risks associated with physically entering the patient, it potentially has less risk than the procedures in current use, e.g., by virtue of the fact that a craniotomy is not performed. Accordingly, aneurysms that would otherwise just be surveilled might instead be treated by the disclosed methods without increasing risk to the patient. For example, the presently disclosed methods contemplate that some smaller aneurysms that would otherwise be surveilled can justifiably be treated, thereby preventing a potential rupture. As another example, aneurysms at locations that are relatively difficult to reach by current surgical methods may instead be treated by radiosurgery. Thus, aneurysms of the posterior fossa are more difficult to clip than aneurysms of the anterior circulation, so the former aneurysm might be treated with stereotactic radiosurgery rather than clipping. Or because tortuous vessels may make it difficult to access some aneurysms endovascularly, or if the aneurysm is located at a site that is dangerously close to vital anatomic regions, or if the patient is unable to tolerate conventional operative intervention, the aneurysms may instead be treated by stereotactic radiosurgery.

A second motivation for the present disclosure is the inventor's recognition that the objective of the stereotactic radiosurgery need not be the obliteration of the aneurysm. The present objective is instead to impede the progression of the aneurysms towards rupture. Thus, if the aneurysm is obliterated by the stereotactic radiosurgery, then the progression towards rupture is inherently retarded. But if the stereotactic radiosurgery causes the aneurysm to be maintained in an innocuous state without obliteration, then the invention's objective is also satisfied. And if an aneurysm is obliterated by the procedure, a further objective of the invention is to prevent or delay the recurrence of an aneurysm at that site.

Finally, the use of stereotactic radiosurgery and coil embolization should be regarded as potentially complementary, rather than mutually exclusive for treating an unruptured aneurysm. The present invention may use radiosurgery to target the lumen of coil-embolized intracranial aneurysms to facilitate thrombosis and scarring for aneurysm occlusion and to reduce the incidence of recanalization. The present invention may also use radiosurgery to target the lumen of coil-embolized intracranial aneurysms that have demonstrated recurrence, to promote thrombosis and scarring for re-occlusion.

It should also be noted that the use of stereotactic radiosurgery to treat an unruptured saccular aneurysm is counterintuitive, considering what is presently known about the mechanisms of aneurysm growth and rupture. Hemodynamic analysis indicates that flow-induced wall shear stress plays a fundamental role in the growth of aneurysms. The response to that stress is myointimal hyperplasia, whereby an arterial wall responds not only to hemodynamic stress, but also to other forms of injury as well, in a process collectively known as vascular remodeling [Gary H. GIBBONS, and Victor J. Dzau. The Emerging Concept of Vascular Remodeling. N Engl J Med 330(1994):1431-1438; HERITY N A, Ward M R, Lo S, Yeung A C. Review: Clinical aspects of vascular remodeling. J Cardiovasc Electrophysiol. 10 (7, 1999): 1016-1024]. In myointimal hyperplasia, proliferation and migration of vascular smooth muscle cells lead to formation of a thickened fibroid layer on the luminal surface of the vessel. The resulting thickening of the wall will alter the geometry of the aneurysm, which in turn will alter the hemodynamics of the flow of blood into and out of the aneurysm, which will in turn alter (and possibly increase) the wall shear stress, leading to an interplay that causes to aneurysm to dynamically change its structure. During the hyperplasia, the vascular smooth muscle cells that migrate from the vascular wall to the luminal surface secrete matrix metalloproteinases that destroy parts of the wall matrix and make the migration of smooth muscle cells possible. But if the destruction of the vessel wall, aided by any inflammatory response, weakens the wall more than the hyperplasia thickens and strengthens the wall, rupture will eventually occur when the wall stress exceeds the wall strength. It is not readily apparent why deliberately causing additional injury to the aneurysm wall using ionizing radiation would not actually promote rupture of the aneurysm, instead of impeding progression of the aneurysm towards rupture. Furthermore, radiotherapy (including whole brain exposure and brachytherapy), is known to have produced aneurysms that did not exist before the radiotherapy [NANNEY A D 3rd, El Tecle N E, El Ahmadieh T Y, Daou M R, Bit Ivan E N, Marymont M H, Batjer H H, Bendok B R. Intracranial aneurysms in previously irradiated fields: literature review and case report. World Neurosurg 81 (3-4, 2014): 511-519].

SUMMARY OF THE INVENTION

Stereotactic radiosurgery (SRS) is used to treat unruptured saccular aneurysms in the brain of a patient. The treatment is intended to impede a natural progression of the aneurysm towards rupture, which may be accomplished by obliterating the aneurysm, although obliteration is not the only way that the impediment can be accomplished.

In the embodiment of the invention that is described here, the radiosurgery is performed using Leksell Gamma Knife® Perfexion™, Leksell® Coordinate Frame G, and Leksell GammaPlan® for Perfexion™. However, the invention contemplates that other types of Gamma Knife devices could be used, as well as Linear Accelerator (LINAC) devices such as the CYBERKNIFE® (Accuray, Sunnyvale, Calif.), NOVALIS Tx™ (BrainLab, Germany), XKNIFE™ (Integra, New Jersey), and AXESSE™ (Elekta, Sweden) stereotactic radiosurgery apparatus, (among others); and charged particle-beam devices. The radiosurgery could involve a single session of treatment, or the treatment dose could be fractionated throughout more than one session. Proper use of the equipment requires that certain calibration and quality assurance steps be performed on a routine basis.

The following steps are taken in the invention: The aneurysm is identified and characterized; a head frame is placed on the patient; three-dimensional imaging of the aneurysm and its anatomical environment is performed, typically using magnetic resonance angiography without or with IV contrast, and/or computed tomography angiography with IV contrast, and/or digital subtraction cerebral angiography; computer-aided dose planning is performed; radiation is delivered to the patient's aneurysm according to the plan; and a post-radiation evaluation of the patient is performed.

Substeps of the step "computer-aided dose planning" are as follows: three-dimensional images of the aneurysm and its environment are imported into the computer that is used to perform the dose planning; the images of the aneurysm are placed in register with one another; the registered images are then used to contour the aneurysm, i.e., define the boundary of the aneurysm within which radiation is to be delivered, as well as critical structures that should be avoided when planning the shots, such as nearby nerves and the parent artery to which the aneurysm is attached (which must always remain open so as to prevent a stroke); a radiation dose is then prescribed for the patient, which involves deciding a 50% isodose-curve determined by the number of radiation shots, shot locations, shot sizes, and shot weights, wherein the shot sizes are determined in part by selection of apertures for the beams, and the shot weights are determined in part by the selected beam-on duration of each shot; and after possible modification of an initial radiation dose prescription, the final dose prescription is made.

The aneurysm may be detected incidentally during the diagnosis or treatment of some other brain disorder, or it may be detected through screening. Specialized imaging methods may be used to characterize the aneurysm in detail, providing information that can be used in planning the treatment. Those methods may provide information about the following features of the aneurysm: permeability, wall thickness, wall motion, the presence of macrophages, shear stress, flow velocities, and the anatomical substructures of the aneurysm. In addition, a morphological analysis of the aneurysm can be used in planning the treatment. In general, the morphological analysis characterizes the shape of the aneurysm, preferably with enough morphological features (dome height, dome diameter, neck width, etc.) to allow a good approximate reconstruction of the shape of the aneurysm, given only the set of extracted morphological features. The measured morphology of the aneurysm may be used to estimate shear forces and blood flows by first solving the Navier-Stokes equations of fluid mechanics that correspond to the measured morphology.

The treatment plan is a prescribed dose distribution conformal to the target (50% isodose-curve determined by the number of shots, shot locations, shot sizes, shot weights). It can be complex by virtue of the combination of shots using different combinations of apertures and weights (beam-on time). In the simplest plan, the radiation is simply directed to the volume defined by the outer contour of the aneurysm, with a rapid fall-of of radiation outside that volume, and with preferential avoidance of any beam being directed to the critical structures (e.g., nerves, as well as the parent artery to which the aneurysm is attached, so as to prevent occlusion of the artery). The plan may also direct the radiation to some specific part of the aneurysm (e.g., dome, body or neck). Conceivably, the plan may even direct radiation to a vessel to which the aneurysm is attached, e.g., if the vessel itself is abnormal, or if alteration of blood flow patterns within the parent vessel is being attempted as a form of flow diversion.

The decision concerning which part(s) of the aneurysm to irradiate is based in part upon a model that predicts the likelihood of not causing a rupture of the aneurysm. Input to the model is the set of characteristics that had been measured to characterize the aneurysm, as well as a database of outcomes for aneurysms that had been treated in the past. The model may make use of prediction methods, such as a support vector machine. For any plan, computer-based optimization techniques may be used to determine isocenters, the shot shapes, and the dose intensity (radiation duration at an isocenter), in lieu of having the physician assign the shots manually. The optimization methods may involve mathematical techniques such as sphere packing, dynamic programming, simulated annealing, mixed integer programming and nonlinear programming. But ultimately, the radiosurgeon must decide the extent to which such computer-based techniques provide reasonable results, and modify the plan accordingly.

Stereotactic radiosurgery that delivers ionizing radiation to the aneurysm would facilitate clot formation and prevent recurrence by the following mechanisms: (1) Lesions to the tunica intimata, to create a thrombotic surface along the inner wall of the aneurysm dome; to injure antithrombogenic endothelial cells that foster the activation of enzymes involved in clot removal; and to promote neointimal proliferation and recruitment of smooth muscle cells for progressive narrowing and occlusion of the aneurysm dome. (2) Lesions to the tunica adventitia: to activate the proliferation of cells at that location, which facilitates neointimal occlusion; and (3) Lesions to the wall (tunica intimata and tunica adventitia) of the aneurysm to induce radiation necrosis and fibrosis for permanent obliteration.

The novel systems, devices and methods for diagnosing and treating conditions using the disclosed devices are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings. It should be understood that application of the methods and devices is not limited to examples that are given. Users of a Linear Accelerator (LINAC) device such as the CYBERKNIFE® stereotactic radiosurgery apparatus (Accuray, Sunnyvale, Calif.) will understand that with such a device one can use non-isocentric targeting that allows for prescription to the 90th percentile isodose line. As mentioned above, a stereotactic head frame would also not be needed because the bony landmarks on the CAT scan serve as targeting reference points. On the day that the imaging studies are performed, the CYBERKNIFE® stereotactic radiosurgery apparatus patient is also fitted with a custom Aquaplast mask, which serves to keep the patient immobile during the treatment. If a coil is already present in the aneurysm, a simple two dimensional CT scan may be sufficient for imaging purposes.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentality shown, but rather only by the claims.

FIG. 2 provides a flowchart for sub-steps involved in the step shown in FIG. 1 as "computer-aided dose planning."

FIG. 3 shows properties of the aneurysms that may be used to plan the stereotactic radiosurgery of the invention.

DETAILED DESCRIPTION OF THE PREFERRED EMBODIMENTS

Figure 1:
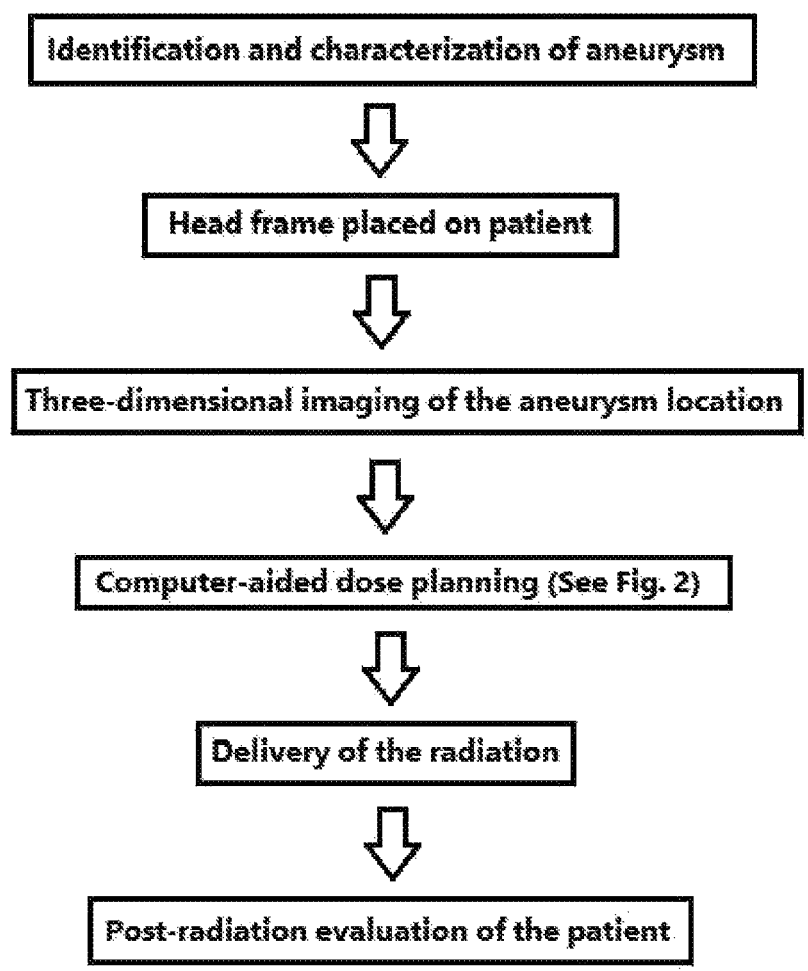
FIG. 1 is a flowchart for performing stereotactic radiosurgical steps of the invention.

Three types of radiosurgical devices have been used for stereotactic radiosurgery (SRS)—the Gamma Knife stereotactic radiosurgery apparatus (Elekta, Sweden); Linear Accelerator (LINAC) devices such as the CYBERKNIFE® (Accuray, Sunnyvale, Calif.), NOVALIS Tx™ (BrainLab, Germany), XKNIFE™ (Integra, New Jersey), and AXESSE™ (Elekta, Sweden) stereotactic radiosurgery apparatus, (among others); and proton beam devices. Because the Gamma Knife is the oldest and arguably best known such device, the description of the invention that follows presumes that it makes use of the Gamma Knife device, but without endorsing its use over other SRS devices. To give a specific embodiment of the invention, the specific radiosurgical equipment could comprise a Gamma Knife device, stereotactic frame, and planning software, respectively, as follows: Leksell Gamma Knife® Perfexion™ (Catalog No. 715000), Leksell® Coordinate Frame G (Catalog No. 1006442), and Leksell GammaPlan® for Perfexion™ (Catalog No. 1006938), along with accessories for stereotactic radiosurgery that are described in the Neuroscience Products and Services Catalog of Elekta Instrument AB, Box 7593, Tungsten 18, SE-103 93 Stockholm, Sweden. It is understood that practitioners of SRS would know to modify the disclosed procedures if a different SRS device were available to them, for example, by eliminating or modifying steps involving a stereotactic head frame if their SRS device uses robotics (e.g., industrial robotic arm used in the CYBERKNIFE® stereotactic radiosurgery apparatus), in which real-time imaging is performed to track the location of the target tissue as treatment is performed, thereby eliminating the need for a stereotactic head frame.

Certain distinctive features of the exemplary Perfexion Gamma Knife equipment should be understood, in order to appreciate how it differs from other Gamma Knife devices, as well as from Linear Accelerator and charged-beam radiosurgical devices [patents U.S. Pat. No. 6,931,096, to CARLSSON et al., entitled Radiation therapy device; U.S. Pat. No. 6,968,036, to CARLSSON et al., entitled Radiation therapy device; U.S. Pat. No. 7,313,222, to CARLSSON and Hedin, entitled Method at a radiation therapy system]. Within a shielded vault, the beams of gamma rays from 192 Co-60 sources are focused so that they intersect at a single location. As with other Gamma Knife devices, the beams produce an elliptical region of high radiation dose when used in their default mode of operation, with a rapid falloff in dose outside the boundary of the ellipse. Each time a radiation exposure is made, the exposure is known as a shot of radiation. To treat irregularly shaped anatomical objects, several shots of radiation are often used, each of which generally has its own highest intensity center within the anatomical object. The centers of the several shots that are directed towards a particular anatomical object are generally close to one another, and the radiation administered to any part of the object is the sum of any overlapping elliptical shots of radiation. Consequently, the dose of radiation experienced by an anatomical object is determined in part by the number and geometry of the potentially overlapping shots of radiation, in addition to the duration of each shot.

Another factor that determines the dose is the diameter of each of the beams of radiation that intersect at the treatment location. A distinctive feature of the Perfexion Gamma Knife is that the Co-60 sources are not fixed in space. Instead, they reside on 8 movable sectors of a collimator system. The collimator system defines the diameter of each of the beams. Apertures of the Perfexion collimator system allow for 4 mm, 8 mm, and 16 mm treatment beams, which are selected by the radiosurgeon through a planning process that is described below. The radiosurgeon may also block a beam, so that the absence of a potential treatment beam is also contemplated.

The collimator is partitioned into 8 independently movable sectors, each of which delivers 24 beams of radiation. Beam size can be changed dynamically for each sector. Individual sectors can also be blocked to help shape each shot of radiation, and in principle each beam within a sector could also be blocked, although that would have to be done manually rather than relying on automation of the device, which uses motors to mechanically set all the apertures of a sector to the same aperture size (or to blockage). Consequently, another factor that determines the administered dosage is the set of aperture sizes that have been selected for each beam for each shot of a given duration. In fact, the most distinctive capability of the Perfexion Gamma Knife is the ability to generate a single isocenter composed of different beam diameters. Such a composite shot design allows an optimized dose distribution shape for each individual shot.

Two other aspects of the Perfexion Gamma Knife system should be mentioned at this point. The first pertains to the use of fractionated doses. Radiotherapy that is split into successive treatment sessions on different days is said to be delivered in fractions. Delivering a small fraction of the total radiation dose allows time for cells to adapt between treatments, and the overall treatment plan may be designed to exploit that adaptation. For a fractionated protocol to succeed, it is necessary to be able to accurately re-position the patient for each fraction. The manufacturer of the Perfexion Gamma Knife system has developed apparatus called eXtend™ that is designed for this purpose, which comprises a stereotactic head frame with a vacuum-assisted bite block. The other aspect of the system that should be mentioned is that proper use of the equipment requires that certain calibration and quality assurance steps be performed on a routine basis [SEUNG S K, Larson D A, Galvin J M, Mehta M P, Potters L, Schultz C J, Yajnik S V, Hartford A C, Rosenthal S A. American College of Radiology (ACR) and American Society for Radiation Oncology (ASTRO) Practice guideline for the performance of stereotactic radiosurgery (SRS). Am J Clin Oncol. 36 (3, 2013): 310-315].

A flowchart for performing steps of the invention is shown in FIG. 1. Those sequential steps comprise identification and characterization of the aneurysm; placement of a head frame on the patient; three-dimensional imaging of the aneurysm and its environment; computer-aided dose planning; delivery of the radiation; and post-radiation evaluation of the patient. Each of those steps will now be summarized. Then, one step of the procedure will be described in more detail, namely, the one involving computer-aided dose planning.

Identification and Characterization of the Aneurysm.

An aneurysm may be detected incidentally during the diagnosis or treatment of some other brain disorder. Some high-risk patients may have had their aneurysm detected during a screening specifically for aneurysms. The patients at highest risk are those for whom aneurysms run in their families, and those exhibiting certain conditions such as systemic lupus erythematosus, genetic disorders such as autosomal dominant polycystic kidney disease, and those having previously ruptured aneurysms. The at-risk patients should begin screening in their twenties and have repeated screening every 5 to 10 years thereafter. Three dimensional time-of-flight magnetic resonance angiography or computed tomography angiography may be used as non-invasive imaging methods for screening. However, catheter angiography, preferably using digital subtraction, is the gold standard when it is clinically imperative to know whether an aneurysm exists. Any individuals exhibiting or being at high risk for a brain aneurysm should carefully control high blood pressure, stop smoking, and avoid cocaine use or other stimulant drugs. They should also be counseled about the benefits and risks of taking aspirin or other drugs that thin the blood. Women should be counseled about the use of oral contraceptives [Hae Woong JEONG, Jung Hwa Seo, Sung Tae Kim, Cheol Kyu Jung, and Sang-il Suh. Clinical practice guideline for the management of intracranial aneurysms. Neurointervention 9(2014):63-71].

Figures 3A, 3B:
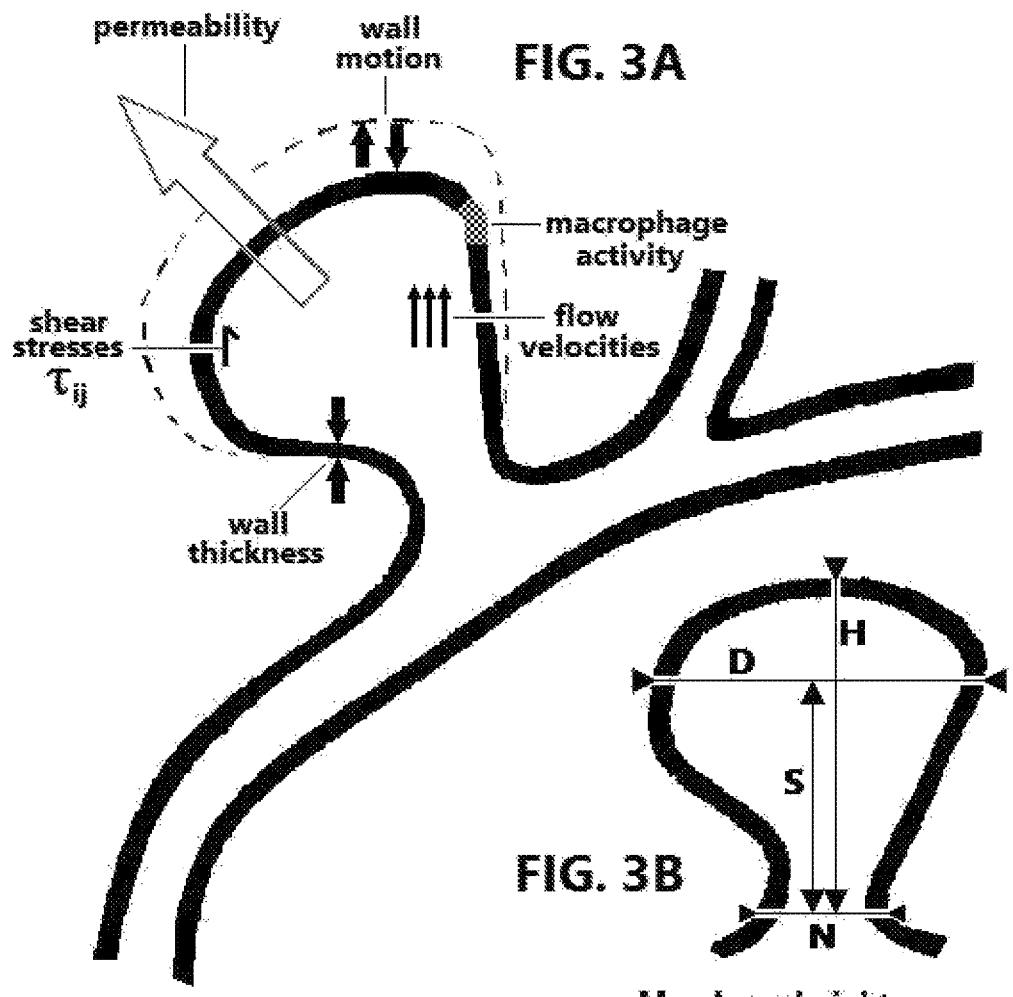
FIG. 3A shows properties of the aneurysms that may be measured using special imaging methods for purposes of planning the stereotactic radiosurgery, namely, permeability, wall thickness, wall motion, the presence of macrophages, shear stress, and flow velocities.
FIG. 3B shows morphological features of aneurysms that are commonly used to characterize the geometry of an aneurysm, which (along with additional possible morphological features) may also be used to plan the stereotactic radiosurgery.

Specialized imaging methods may be used to characterize the aneurysm and its growth in detail, using measured properties that are indicated in FIG. 3A. The data corresponding to that characterization may be used to predict whether a particular irradiation plan would possibly cause the aneurysm to rupture, as described below. For example, aneurysm wall permeability can be quantified using dynamic contrast-enhanced (DCE)-MRI and the perfusion parameter Ktrans, which is a size-independent predictor of rupture risk. High field-strength 7 T MRI scanners have the spatial resolution needed to detect variations in aneurysm wall thickness, which may be a marker of rupture risk. Another advanced imaging technique combines MRA with postprocessing algorithms from computational fluid dynamics to create 4D flow modeling. Time-resolved MRA directly measures flow velocities and shear stresses within an aneurysm. Arterial wall motion abnormalities may be detected using phase-contrast MRA, transcranial power Doppler ultrasonography, 4D-CTA, and 3D rotational angiography. MRI imaging after ferumoxytol infusion can provide an indication of macrophage activity and inflammation within the aneurysm and its adjacent vessels. If the grading of the aneurysm is such that it may not be an immediate cause for concern, it may be useful to repeat the imaging at approximately 6 month to 1 year intervals in order to estimate the rate and manner of aneurysm growth [VAKIL P, Ansari S A, Cantrell C G, Eddleman C S, Dehkordi F H, Vranic J, et al. Quantifying intracranial aneurysm wall permeability for risk assessment using dynamic contrast-enhanced MRI: A pilot study. AJNR Am J Neuroradiol 36(2015):953-959; KLEIN-LOOG R, Korkmaz E, Zwanenburg J J, Kuijf H J, Visser F, Blankena R, et al. Visualization of the aneurysm wall: a 7.0-tesla magnetic resonance imaging study. Neurosurgery 75(2014):614-622; VANROSSOMME A E, Eker O F, Thiran J P, Courbebaisse G P, Zouaoui Boudjeltia K. Intracranial aneurysms: Wall motion analysis for prediction of rupture. AJNR Am J Neuroradiol 36(2015):1796-1802; CEBRAL J R, Vazquez M, Sforza D M, Houzeaux G, Tateshima S, Scrivano E, et al. Analysis of hemodynamics and wall mechanics at sites of cerebral aneurysm rupture. J Neurointery Surg 7(2015):530-536; SCHNELL S, Ansari S A, Vakil P, Wasielewski M, Carr M L, Hurley M C, et al. Three dimensional hemodynamics in intracranial aneurysms: influence of size and morphology. J Magn Reson Imaging 39(2014):120-131; BOUSSEL L, Rayz V, Martin A, Acevedo-Bolton G, Lawton M T, Higashida R, et al. Phase-contrast magnetic resonance imaging measurements in intracranial aneurysms in vivo of flow patterns, velocity fields, and wall shear stress: comparison with computational fluid dynamics. Magn Reson Med 61(2009):409-417; Michael R. LEVITT, M. Yashar S. Kalani, Karam Moon, Cameron G. McDougall, Felipe C. Albuquerque. Advances in the imaging of cerebral aneurysm inflammation. Neuroimmunol Neuroinflammation 2 (2, 2015): 51-54; Tiffany Y. S O, Richard Dowling, Peter J. Mitchell, John Laidlaw, Bernard Yan. Risk of growth in unruptured intracranial aneurysms: A retrospective analysis. Journal of Clinical Neuroscience 17(2010):29-33].

The imaging should also show sufficient detail to be able to accurately estimate the location, size and morphology (e.g., aspect ratio), and rupture status of any aneurysm that is detected. FIG. 3B shows morphological features of aneurysms that are commonly used to characterize the geometry of an aneurysm [Luciana PARLEA, Rebecca Fahrig, David W. Holdsworth, and Stephen P. Lownie. An Analysis of the Geometry of Saccular Intracranial Aneurysms. AJNR Am J Neuroradiol 20(1999):1079-1089]. Examples of additional geometric features are the volume and surface area of the aneurysm. In order to implement methods that are described below, the number of morphological features that are extracted from the images should be sufficient to allow the approximate reconstruction of the morphology of the aneurysms, given only the set of extracted morphological features. For example, the shape of the aneurysm may also be approximated by the coefficients in a truncated expansion, and those coefficients serve as morphological features that may be used to compare the shape of one aneurysm with another, or the same aneurysm at successive times, thereby characterizing its progression [Dengsheng ZHANG, Guojun Lu. Review of shape representation and description techniques. Pattern Recognition 37(2004):1-19]. Such coefficients would ordinarily not be estimated until after the images had been contoured to establish the boundaries of the aneurysm, as described below. The reconstruction of the morphology should be good enough to distinguish a smooth aneurysm dome from a nodular dome. If imaging has not been performed to measure shear stress and flow velocities, those parameters may nevertheless be estimated from the geometry of the aneurysm alone, by numerical calculations of the Navier-Stokes equations of fluid mechanics. As described by CEBRAL et al., after solving the Navier-Stokes equations of fluid mechanics, it is possible to extract additional parameters that characterize the physical properties of the aneurysm [J. R. CEBRAL, F. Mut, J. Weir, C. Putman. Quantitative Characterization of the hemodynamic environment in ruptured and unruptured brain aneurysms. AJNR Am J Neuroradiol 32(2011):145-151].

A Head Frame is Placed on the Patient.

In the presently disclosed embodiment, the Leksell® Coordinate Frame G (Catalog No. 1006442) is attached to the patient under local anesthesia [patent U.S. Pat. No. 8,221,435, to ARNDT, Nilsson and Olsson, entitled Device comprising a pin support member and insulation means for fixation to a patients skull during neurological diagnosis, and a method for assembling said device]. Techniques for attaching the stereotactic head frame to the patient's head are described in the following publication, which is incorporated by reference: SAFAEE M, Burke J, Mcdermott M W. Techniques for the Application of Stereotactic Head Frames Based on a 25-Year Experience. Cureus 8 (3, 2016): e543. DOI 10.7759/cureus.543, pp. 1-15.

Three-Dimensional Imaging of the Aneurysm and its Anatomical Environment.

After the head frame is attached, the patient undergoes brain imaging so that the location of the aneurysm can be precisely mapped for planning the treatment, using a fiducial box attached to the patient's stereotactic head frame. The three-dimensional brain imaging procedure can be at least one of: magnetic resonance angiography without or with IV contrast, computed tomography angiography with IV contrast, and digital subtraction cerebral angiography [Nam K. YOON, Scott McNally, Philipp Taussky and Min S. Park. Imaging of cerebral aneurysms: a clinical perspective. Neurovascular Imaging 2:6 (2016) DOI: 10.1186/s40809-016-0016-3, pp. 1-7]. Those standard imaging methods may be supplemented by any of the more specialized imaging methods that are recited above in connection with the characterization of the aneurysm prior to the decision to proceed to treatment.

Computer-Aided Dose Planning.

Computer-aided dose planning involves importing the three-dimensional images of the aneurysm and its environment; placing the images in register with one another; contouring the structures that are to be irradiated (and structures that should not be irradiated); defining, possibly modifying, and evaluating the irradiation dose prescription; and approving the planned radiation treatment for delivery. These steps are described in detail in connection with FIG. 2. Certain aspects of the planning are specific to the particular machine that is being used, because the planning involves the selection of aperture sizes and aperture blockages that are intended to shape the location and dosage of each shot for that particular machine. In the presently described embodiment, the Leksell GammaPlan® for Perfexion™ (Catalog No. 1006938) software may be used for planning the dose in relation to changing individual sector collimator sizes. That software allows for the incorporation of add-on software modules, such as an inverse planning module, as well as custom modules that instantiate methods that are disclosed herein [SHEPARD D M, Ferris M C, Ove R, Ma L. Inverse treatment planning for Gamma Knife radiosurgery. Med Phys 27(12, 2000):2748-2756].

Delivery of the Radiation.

A patient positioning system (PPS) in the Leksell Gamma Knife® Perfexion™ system is used to position the patient for radiosurgery. A frame adapter attaches the Leksell coordinate frame (affixed to the patient's skull) to a treatment couch. With the Perfexion PPS, instead of moving only the patient's head, the whole body of the patient lying on the PPS couch is moved into the pre-selected stereotactic coordinates. Thus, doors to the treatment unit open, and the patient is advanced into the shielded treatment vault, whereupon the Perfexion automatically exposes the patient to the shots that had been planned using the Leksell GammaPlan® for Perfexion™ software. Post-surgery, the frame is removed from the patient. Bandages and antibiotic ointments are used to treat any drainage from sites on the patient's skin corresponding to the pins of the SRS frame. A prescription for dexamethasone (Decadron®) may be provided to decrease the risk of swelling of the brain.

Post-Radiation Evaluation of the Patient.

Following the irradiation, aspirin may be considered as an anti-inflammatory drug [Robert M. STARKE, Nohra Chalouhi, Dale Ding, and David M. Hasan. Potential role of aspirin in the prevention of aneurysmal subarachnoid hemorrhage. Cerebrovasc Dis 39 (0, 2015): 332-342]. The post-radiation evaluation of the patient involves the same imaging methods that were used for the identification and characterization of the patient, except that the imaging may be performed within 3 to 6 months after the treatment. Thereafter, it may be useful to repeat the imaging at approximately 6 month to 1 year intervals in order to estimate the rate and manner of aneurysm regression (or growth).

FIG. 2 provides a flowchart for substeps involved in the step shown in FIG. 1 as "computer-aided dose planning." The substeps comprise importing the three-dimensional images of the aneurysm and its environment; placing images in register with one another; contouring the structures that are to be irradiated; defining, possibly modifying, and evaluating the irradiation dose prescription (including any planned fractionation schedule, which would ordinarily be from 1 to 5 doses); and finally, approving the planned radiation treatment for delivery. Those substeps are now described in what follows.

Importing the Three-Dimensional Images of the Aneurysm and its Environment

The images of the aneurysm and its anatomical environment, comprising one or more three-dimensional images acquired using one or more of the above-mentioned imaging modalities, are moved from their disc storage location into the memory of a digital computer of suitable size and power, in order to perform the registration, contouring, and dose-prescribing steps that follow. As described above in connection with "Identification and characterization of the aneurysm," the imaging modalities may include magnetic resonance angiographic images, computed tomography angiographic images, digital subtraction angiographic images, high resolution images that show the varying thickness of the wall of the aneurysm and its adjacent blood vessel(s), images of aneurysm wall permeability, directly measured or inferred flow velocities and shear stresses within the aneurysm, motion of the aneurysm wall and its adjacent blood vessel(s), and images of macrophage activity and inflammation within the aneurysm and its adjacent vessel(s).

Placing the Images in Register with One Another

Because the above-mentioned images may have been acquired using different imaging modalities, it is first necessary to combine them into a single unified data set, in which the same anatomical location in each image is superimposed upon the corresponding location in all the other images. Algorithmic methods for placing the images in register with one another are described in: Derek L G HILL, Philipp G Batchelor, Mark Holden and David J Hawkes. Medical image registration. Phys. Med. Biol. 46 (2001): R1-R45; J. B. Antoine MAINTZ and Max A. Viergever. An Overview of Medical Image Registration Methods. In: Proceedings of the 1996 Symposium of the Belgian hospital physicists association (SBPH-BVZF), Vol 12, pp. V:1-22. 1996.

Contouring the Structures that are to be Irradiated

The next step is to extract from the registered images the contours of the aneurysm and its parts, along with contours of the blood vessel(s) to which the aneurysm is attached. The blood vessels would ordinarily be considered to be critical structure that should not be irradiated, so the contouring consists of defining the target and critical structures. Examples of other critical structures to be avoided are the brain stem, optic nerve and other cranial nerves. Another term for the contouring is segmenting the image into the region(s) of interest, which is the process of assigning a label to every voxel in an image such that voxels with the same label share certain characteristics. The boundaries where voxels corresponding to one characteristic change to another characteristic constitute a set of contours for the image. In conventional stereotactic radiosurgery, one or more closed contours define the volume in which the radiation shots are to be delivered. Conventionally, one or more other closed contours also define volumes containing critical structures that should be avoided when planning the shots, such as nearby nerves. In the present context, one would generally wish to avoid irradiating the parent vessel because the result may be occlusion of the vessel and a subsequent stroke. In that regard, use of inverse planning may facilitate avoiding the irradiation of critical structures.

In the present disclosure, a voxel within or along the surface of a contour may have additional data associated with it. For example, if a contour corresponds to the outer surface of an aneurysm, the invention contemplates associating with each such voxel the data corresponding to the above-mentioned measured properties such as permeability, wall thickness, the magnitude of wall motion, and the presence of macrophages. Similarly, if a contour corresponds to the inner surface of an aneurysm, the invention contemplates associating with each such voxel the data corresponding to measured properties such as shear stress. The contour of the inner surface of the aneurysm will also define the boundary of the lumen of the aneurysm, and each voxel within the lumen may have associated with it measured properties such as flow velocities. Voxels along the inner and outer contours of the aneurysm may also be associated with a binary variable corresponding to whether the voxel corresponds to a segment of the aneurysm neck or not. The vessel(s) to which the aneurysm is attached may be similarly contoured. Thus, the output from this step is a model of the relevant anatomy of the aneurysm and its attached blood vessel(s) expressed in three-dimensional coordinates from the stereotactic frame, along with data corresponding to such properties as permeability, wall thickness, wall motion, the presence of macrophages, shear stress, flow velocities, and the anatomical substructures of the aneurysm.

The most straightforward method for defining the contours of the aneurysm is to have an expert human trace the outer surface of the aneurysm throughout the three-dimensional images, as well as the surface of the lumen if the imaging has been done with sufficient resolution. Semi-automated methods may also be used, in which image processing methods such as edge detection are used, or even completely automated methods if they have been adequately validated. For example, the contours defined by an expert human may be used as a training set for machine learning algorithms, which are then applied to test sets of images. The machine learning algorithms will then define the contours within the test images automatically [Nisreen SULAYMAN, Moustafa Al-Mawaldi, Qosai Kanafani. Semi-automatic detection and segmentation algorithm of saccular aneurysms in 2D cerebral DSA images. The Egyptian Journal of Radiology and Nuclear Medicine 47(2016):859-865].

Defining, Possibly Modifying, and Evaluating the Irradiation Dose Prescription.

In this step, the planner specifies the sites where the radiation is to be focused by placing shots. The final plan is a specification of many shots, and the end result is a prescribed dose distribution conformal to the target (50% isodose-curve determined by the number of shots, shot locations, shot sizes, shot weights). It can be complex by virtue of the combination of shots using different combinations of apertures and weights (beam-on time). In the simplest plan, the radiation is simply directed to the volume defined by the outer contour of the aneurysm, with a rapid fall-of of radiation outside that volume, and with preferential avoidance of any beam being directed to the critical structures (nerves, etc.). With such a plan, optimization techniques may be used to determine isocenters, the shot shapes, and the dose intensity (radiation duration at an isocenter), in lieu of having the physician assign the shots manually.

Optimization methods may involve mathematical techniques known as sphere packing, dynamic programming, simulated annealing, mixed integer programming and non-linear programming [A. SUTOU and Y. Dai. Global optimization approach to unequal sphere packing problems in 3D. Journal of Optimization Theory and Applications 114 (3, 2002): 671-694; Hamid R. GHAFFARI. Optimization models and techniques for radiation treatment planning applied to Leksell Gamma Knife Perfexion. PhD Thesis. Department of Mechanical and Industrial Engineering. University of Toronto. 2012. pp. 1-116]. In the presently described embodiment, the Leksell GammaPlan® for Perfexion™ (Catalog No. 1006938) software is used for planning the dose in relation to changing individual sector collimator sizes [patent application U.S. Ser. No. 12/444,021 published as US20090306483, to GARDING, Kjall, and Lidberg, entitled Treatment planning systems]. That software allows for the incorporation of add-on software modules, such as an inverse planning module, as well as custom modules that instantiate methods that are disclosed herein.

The conventional methods for defining an irradiation dose prescription, as described above, would not make use of more information than the location of the outer surface of the aneurysm. In the present invention, in addition to the objective of such things as optimally packing spheres of radiation shots into a volume of interest, there is also the objective of estimating, for any potential irradiated volume of interest, the likelihood that the corresponding shots of radiation will impede a natural progression of the aneurysm towards rupture. A special case of that estimation is an additional estimation of the probability that the aneurysm becomes obliterated following the treatment.

In order to estimate such probabilities, a model is used (empirical, conceptual, or mathematical) that explains or predicts what will happen to the aneurysm if a particular volume of interest is irradiated. The volume of interest may be the entire aneurysm or a portion of the aneurysm. Conceivably, the plan may even direct radiation to a vessel (s) to which the aneurysm is attached, e.g., if the vessel itself is abnormal, or if alteration of blood flow patterns within the parent vessel is being attempted as a form of flow diversion. It is known that saccular aneurysm formation and growth is highly dependent on the geometry (angles and sizes) of parent arteries at the point of arterial bifurcation. In bifurcations without aneurysms, intimal hyperplasia at the apex is a normal, healthy, developmental response of a vessel subjected to flow impingement, which leads to the formation of intimal pads that modify the hemodynamics at that location [MENG H, Wang Z, Hoi Y, Gao L, Metaxa E, Swartz D D, Kolega J. Complex hemodynamics at the apex of an arterial bifurcation induces vascular remodeling resembling cerebral aneurysm initiation. Stroke 38 (6, 2007): 1924-1931]. In the present invention, it is contemplated that in vessels that do not possess correspondingly protective pads, stereotactic radiosurgery that is directed to the apex or other vessel locations may be used to induce protective hyperplasia, thereby modifying the blood flow to a state that does not promote the growth of an aneurysm or that promotes aneurysm thrombosis. It is understood that the induced hyperplasia must be significantly less than what would cause stenosis and occlusion of the vessel, thereby avoiding the production of a stroke.

Figure 4A:
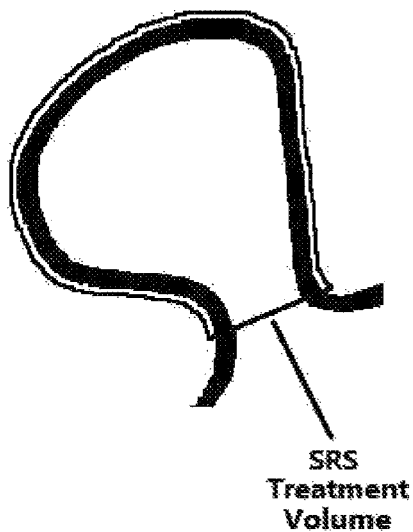
FIG. 4 gives examples of potential irradiated volumes of the aneurysm, which might, among other possibilities, consist of the whole aneurysm (shown in FIG. 4A), the neck area of the aneurysm (shown in FIG. 4B), or the dome area of the aneurysm (shown in FIG. 4C).
Figure 4B:
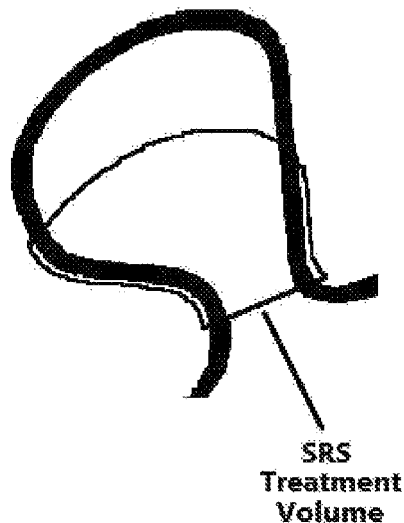
Figure 4C:
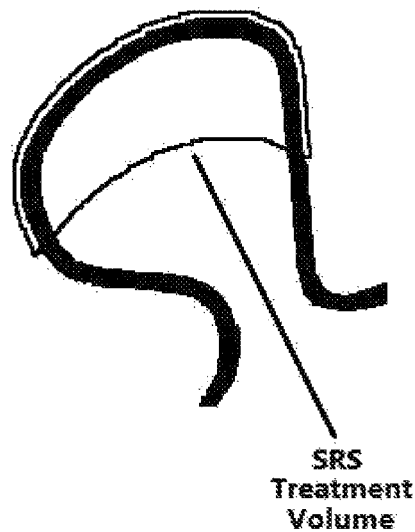

For example, FIG. 4A shows the volume of interest to be the whole aneurysm from the ostium to the top of the dome, FIG. 4B shows the volume of interest to be only the volume nearest the neck of the aneurysm, and FIG. 4C shows the volume of interest to be only the volume nearest the dome of the aneurysm. The volume shown in FIG. 4B may be motivated, for example, by the measurement of an unusual thinning of the aneurysm dome. Consequently, the radiosurgeon may want to avoid radiating the dome for fear of causing further weakening of the dome that could result in a rupture there. On the other hand, there may be circumstances in which the dome itself may be the target of preferential irradiation, as shown in FIG. 4C. Considerations that motivate selection of a particular volume of interest to irradiate may be as follows.

A normal artery wall consists of three layers: the intima, which is the innermost endothelial layer; the media, which consists of smooth muscle; and the adventitia, the outermost layer, which consists of connective tissue. Sometimes, the aneurysmal sac may be composed only of intima and adventitia. The intima is typically normal, although subintimal cellular proliferation is common. The internal elastic membrane may be reduced or absent, and the media may end at the junction of the aneurysm neck with the parent vessel. Lymphocytes and phagocytes may infiltrate the adventitia. Thrombotic debris is often present in the lumen of the aneurysmal sac.

However, intracranial aneurysm lesion presentation is highly heterogeneous, and three principal aneurysm phenotypes have been reported. The first types are small aneurysms (<4 mm) with uniformly thin, smooth, hypocellular, translucent walls, through which blood flow can be visualized at the time of surgical clipping. The second types are entirely thickwalled large aneurysms (>10 mm), with an irregular surface on which plaques obstruct the visualization of blood. The third types are medium-sized aneurysms with a combination of thin- and thick-walled characteristics in different regions. Small intracranial aneurysms (<10 mm) have a higher rate of having thin, transparent, and hypocellular walls; absent smooth muscle cells, and inflammatory cells. Large intracranial aneurysms (>10 mm) have a low rate of thin-walled regions but a high rate of thick walls with atherosclerotic changes, proliferation of smooth muscle cells, and inflammatory cells [H. MENG, V. M. Tutino, J. Xiang, and A. Siddiqui. High WSS or Low WSS? Complex Interactions of Hemodynamics with Intracranial Aneurysm Initiation, Growth, and Rupture: Toward a Unifying Hypothesis. AJNR Am J Neuroradiol 35(2014):1254-1262].

Ruptured aneurysm walls are characterized by loss of mural cells (vascular smooth muscle cells, myofibroblasts, and fibroblasts). In aneurysm walls that have lost their mural cells, the repair and maintenance process maintained by matrix synthesis and proliferation of mural smooth muscle cells is disrupted. Loss of mural cells together with the wear and tear to which collagen fibers are exposed and the proteolytic injury ongoing in some aneurysm walls predisposes the aneurysm wall to rupture. Hence, the loss of mural cells is a key event that leads to the degeneration and eventual rupture of the aneurysm wall [Juhana FROSEN, Riikka Tulamo, Anders Paetau, Elisa Laaksamo, Miikka Korja, Aki Laakso, Mika Niemela, and Juha Hernesniemi. Saccular intracranial aneurysm: pathology and mechanisms. Acta Neuropathol 123 (6, 2012): 773-786]. It is this heterogeneity and progression of aneurysm types that the measurements shown in FIG. 3 are intended to capture or characterize.

Stereotactic radiosurgery that delivers ionizing radiation directed within the aneurysm would produce damage to the aneurysm and cause a physiological response to that damage [HOPEWELL J W, Campling D, Calvo W, Reinhold H S, Wilkinson J H, Yeung T K. Vascular irradiation damage: its cellular basis and likely consequences. Br J Cancer Suppl. 7(1986):181-191; FAJARDO L F, Berthrong M. Vascular lesions following radiation. Pathol Annu. 23 (Pt 1, 1988): 297-330; RODEMANN H P, Blaese M A. Responses of normal cells to ionizing radiation. Semin Radiat Oncol. 17 (2, 2007): 81-88; O'CONNOR M M, Mayberg M R. Effects of radiation on cerebral vasculature: a review. Neurosurgery 46 (1, 2000): 138-149; HALLE M, Hall P, Tornvall P.

Cardiovascular disease associated with radiotherapy: activation of nuclear factor kappa-B. J Intern Med. 269 (5, 2011): 469-477; XU J, Cao Y. Radiation-induced carotid artery stenosis: a comprehensive review of the literature. Interv Neurol. 2 (4, 2014): 183-192].

The irradiation would facilitate clot formation and prevent recurrence by the following mechanisms: (1) Lesions to the tunica intima, to create a thrombogenic surface along the inner wall of the aneurysmal dome; to injure intact antithrombogenic endothelial cells (endothelial cells foster the activation of plasmin, a proteolytic enzyme involved in clot removal); and to promote neointimal proliferation and recruitment of smooth muscle cells for progressive narrowing and occlusion of the aneurysmal dome. (2) Lesions to the tunica aventitia: to activate the proliferation of myofibroblasts which facilitate neointimal occlusion; and (3) Lesions to the wall (tunica intima and tunica aventitia) of the aneurysm to induce radiation necrosis and fibrosis for permanent obliteration.

The mechanisms (1) to (3) are based upon what is known about the intricate biological response of vascular tissue to injury. Vascular injury propels a cascade of events that ultimately leads to a hyperplastic response characterized by neointimal formation. Neointimal formation is the principal cause of post-injury vessel narrowing and occurs in 3 main stages: 1) clot formation; 2) smooth muscle cell recruitment, proliferation, and migration to luminal surface; and 3) extracellular matrix elaboration. [MULLER D W M, Ellis S G, Topel E J. Experimental models of coronary artery restenosis. J Am Coll Cardiol 1992; 19(1992): 418-432; IP J H, Fuster V, Badimon L, et al. Syndromes of accelerated atherosclerosis: role of vascular injury and smooth muscle proliferation. J Am Coll Cardiol 15(1990): 1667-1687; WILENTZ J R, Sanborn T A, Haundenschild C C, et al. Platelet accumulation in experimental angioplasty: time course and relation to vascular injury. Circulation 75(1987): 636-642; Gary H. GIBBONS, and Victor J. Dzau. The Emerging Concept of Vascular Remodeling. N Engl J Med 330(1994):1431-1438; HERITY N A, Ward M R, Lo S, Yeung A C. Review: Clinical aspects of vascular remodeling. J Cardiovasc Electrophysiol. 10 (7, 1999): 1016-1024].

Initially, injury to the endothelium results in endothelial denudation and loss of heparin-like glycosaminoglycans such as heparin sulfate. These proteins are usually produced by intact endothelium and are important in inhibiting growth of underlying smooth muscle cells [CASTELLOT J J Jr, Addonizio M L, Rosenberg R, et al. Cultured endothelial cells produce a heparin-like inhibitor of smooth muscle growth. J Cell Biol 90(1981): 372-377; CAMPBELL G R, Campbell J H. Smooth muscle phenotypic changes in the arterial wall homeostasis: implications for the pathogenesis of atherosclerosis. Exp Mol Path 42(1985): 139-162].

A stable clot is formed through the conversion of fibrinogen to fibrin and polymerization of linked molecules forming a web that retains plasma fractions and cells. During this inflammatory process, vascular, cellular, and humoral reactions occur at the wound site. The next phase is the granulation phase which is characterized by smooth muscle cell and fibroblast migration and proliferation into the injured area. Finally, a remodeling phase involves proteoglycan and collagen synthesis, which replaces early fibronectin as major component of the extracellular matrix [FORRESTER J S, Fishbein M, Helfant R, et al. A paradigm for restenosis based on cell biology: clues for the development of new preventative therapies. J Am Coll Cardiol 1991; 17: 758-769; SCHWARTZ R S, Holmes D Jr, Topol E. The restenosis paradigm revisited: an alternative proposal for cellular mechanisms. J Am Coll Cardiol 20(1992): 1284-1293; CLOWES A W, Reidy M A, Clowes M M. Kinetics of cellular proliferation after arterial injury. I. Smooth muscle growth in the absence of endothelium. Lab Invest 49(1983): 327-333].

The main steps of wound healing are didactically divided into: a) clot formation and inflammation, b) epithelial healing, c) connective tissue healing, and d) wound maturation and remodeling. After attaining a stable clot, through conversion of fibrinogen into fibrin and polymerization of linked molecules forming a web that retains plasma fractions and cells, the inflammatory process takes place. It involves vascular, cellular and humoral reactions at the wound site, and it prepares the region for healing. Healing depends on the creation, by the inflammatory process, of a favorable environment for cellular metabolism via elimination of microorganisms, necrotic tissue and foreign particles. Epithelial healing occurs in which the keratinocytes form a monolayer of cells that migrate to the center of the wound until contact inhibition occurs, resulting in an epithelial seal of the wound area. This kind of healing prevents the ingrowth of irritants and the loss of fluids (nutrients for the connective cells), maintains the hydration of the wound and promotes an increase in wound strength. Connective tissue healing is the most complex and it depends on the stratification of the epithelial layers. The primary cell involved in this healing is the fibroblast that produces collagen and extracellular matrix, which are essential for regeneration and repair. After the initial inflammatory process, the granulomatous tissue, rich in macrophages, gradually becomes a granulation tissue (predominantly fibroblast), which shows that the connective tissue is healing properly. This process finishes when the collagen aggregation is completed and the extracellular matrix becomes hard. Then, maturation of tissue finally occurs.

The wound-healing reactions result in the accumulation of smooth muscle cells within a proteoglycan matrix that narrows and occludes the lumen. Once the vascular defect is secured, clot removal and revascularization may eventually occur. The clot is removed by local digestive enzymes and scavenging macrophages. Finally, revascularization ensues which involves the formation of a neo-endothelial anti-thrombogenic lumen [BAVINZSKI G, Talazoglu V, Killer M, Richling B, Gruber A, Gross C E, Plenk H Jr. Gross and microscopic histopathological findings in aneurysms of the human brain treated with Guglielmi detachable coils. J Neurosurg 91(1999): 284-293; RAYMOND J, Venne D, Allas S, Roy D, Oliva V L, Denbow N, Salazkin I, Leclerc G. Healing mechanisms in experimental aneurysms, I: vascular smooth muscle cells and neointima formation. J Neuroradiol. 26(1999): 7-20].

It is therefore important for the purposes of treating cerebral aneurysms to promote occlusion in addition to preventing revascularization. To do this, it will be necessary to foster a local state of injury and inflammation to help facilitate and maintain aneurysmal occlusion. In addition, interruption of the normal healing or revascularization process can by accomplished by targeting the cells involved in the removal of obstructive debris (macrophages and endothelial cells) and those involved in reforming the endothelial lining (endothelial cells). Studies in canines have shown that endothelial denudation before coil embolization can improve the results of endovascular treatment [Raymond J, Guilbert F, Metcalfe A, Gévry G, Salazkin I, Robledo O. Role of the Endothelial Lining in Recurrences After Coil Embolization Prevention of Recanalization by Endothelial Denudation. Stroke. 35(2004):1471-1475].

However, denudation would be difficult to accomplish in clinical practice and may increase thromboembolic complications as well as increase risks of perforation or rupture. This procedure would be especially dangerous in lesions treated during the acute phase after subarachnoid hemorrhage. Alternatively, radiation-induced injury could be produced safely in a coil-occluded aneurysm without endovascular manipulation. In addition, lesions could be produced in a more precise and uniform manner using SRS.

The actual radiation dose and fractionation schedule that are selected in the present invention are influenced by target volume, tissue type and critical structure exposure to the fall-off dose. The selection also depends in part on whether the radiosurgeon wants to limit the amount of smooth muscle cell atrophy and thrombosis (if obliteration of the aneurysm is not the primary objective), in which case the dose might be typically 17.5-20 Gy. Otherwise, a higher dose of typically 22.5-25 Gy might be administered [J. W. HOPEWELL, D. Campling, W. Calvo, H. S. Reinhold, J. H. Wilkinson and T. K. Yeung. Vascular irradiation damage: Its cellular basis and likely consequences. Br J Cancer 53(Suppl VII, 1986): 181-191]. The linear quadratic equation is the most widely accepted method of fitting the survival of cells following radiation at a given dose D. It is given by $S(D)=\exp[-(\alpha D+\beta D^2)]$, where S is the relative number of surviving cells following a dose of D, and $\alpha$ and $\beta$ describe the linear and quadratic parts of the survival curve. With respect to dosing, the dome of the aneurysm would ordinarily be treated as having a low alpha/beta ratio, as found in slowly growing tumors such as prostate cancer. Traditionally, such tumors require a relatively high dose in either a single or relatively few fractions (i.e., 2-3). Targets with slow replicating cells require a higher dose delivered in a single or few fractions, whereas tumors with fast replicating cells require higher fractionation schedules since the target DNA is susceptible during cell replication to mutation. It is understood that the oxygen effect and the use of chemical protectors and sensitizers may also differentially influence cell survival. In the present case, the target DNA would be found in susceptible cells within the aneurysm, including vascular smooth muscle cells, myofibroblasts, fibroblasts, macrophages, and endothelial cells (with the latter two preferentially damaged as described above to promote occlusion and prevent revascularization). For example, one expects that the effective dose for obliteration will be 20-25 Gy to the 90% isodose line using a CYBERKNIFE® stereotactic radiosurgery apparatus. The limiting factor will be the dose delivered to the parent vessel. As long as vessel irradiation is kept at an innocuous dose, a dose to the aneurysm dome that causes significant damage there should be acceptable if obliteration is the primary objective.

The invention's predictive model will preferably make use of the data that are available from imaging of the aneurysm (e.g., those shown in FIG. 3A: permeability, wall thickness, wall motion, the presence of macrophages, shear stress, flow velocities, and extracted morphological features such as those shown in FIG. 3B that characterize the shape and anatomical substructures of the aneurysm), as well as postulated or established effects of radiation on blood vessels and mechanisms by which aneurysms develop over time. Whether imaging has been performed or not to measure shear stress and flow velocities, those parameters may be estimated from the geometry of the aneurysm alone, by numerical calculations of the Navier-Stokes equations of fluid mechanics. Such calculations may provide additional parameters that characterize the aneurysm [J. R. CEBRAL, F. Mut, J. Weir, C. Putman. Quantitative Characterization of the Hemodynamic environment in ruptured and unruptured brain aneurysms. AJNR Am J Neuroradiol 32(2011):145-151]. Thus, in the present invention, the plan is optimized among all potential plans in which it is predicted that the outcome will be no progression towards rupture of the aneurysm, and all potential plans that do not meet that criterion are excluded from consideration.

It is understood that there will always be some stochastic element to the timing of aneurysm rupture, for the following reason. Intracranial aneurysm rupture has been associated with intense physical activities and accompanying high blood pressure. Large elevations in mean arterial blood pressure during such activities can increase aneurysm wall tension to a level that leads to rupture. An increased heart rate during physical exertion and emotional excitement have also been suspected of contributing to rupture. Because the times at which a patient may exhibit momentarily high blood pressure depend on the daily activities of the patient, the physician can only advise against intense physical activity, but cannot prevent it. Consequently, the model that is described below presupposes that the patient endeavors to avoid any such potentially harmful activity, which would otherwise complicate the effort to make the prediction.

The model for predicting whether or not the administered radiation inhibits progression towards rupture can be developed and tested in the first place using data from experiments involving the treatment of animal aneurysms, and only later using data involving treatment of patients [Ivanilson Alves de OLIVEIRA. Main Models of Experimental Saccular Aneurysm in Animals, Chapter 3, pp. 43-64 In: Aneurysm, Dr. Yasuo Murai (Ed.), InTech, DOI: 10.5772/50310 (2012)]. The modeling and analysis of such data may be performed using any statistical or artificial intelligence or machine learning or optimization methods known in the art, including multivariate statistics and autoregressive models, as well as models that make use of principal components, Kalman filters, wavelet transforms, hidden Markov models, artificial neural networks, and/or support vector machines. In the preferred embodiments of the present invention, support vector machines are used. A support vector machine (SVM) is an algorithmic approach to the problem of classification within the larger context of supervised learning [PRESS, W H, Teukolsky, S A, Vetterling, W T, Flannery, B P. Section 16.5. Support Vector Machines. In: Numerical Recipes: The Art of Scientific Computing (3rd ed.). New York: Cambridge University Press, 2007].

In the present context, a training set of data will have been acquired that includes a database of many experiments and patient cases concerning whether or not an aneurysm has ruptured by a certain time after the experimental treatment (e.g., six months after treatment), with the analysis repeated for other durations as well (e.g., three months and one year). The classification of the aneurysm in each experiment is whether or not rupture has occurred over the specified time interval, and the data used to make the classification (prediction) consist of parameters of the treatment plan that were used, (including critical structure exposure) as well as the characteristics of the aneurysm that had been measured using imaging prior to the treatment (FIG. 3). In the event that the characteristics of the aneurysm have been imaged and measured over the course of several months or years of surveillance, all such measurements are included in the database of measurements to quantify the extent of progression of that particular aneurysm. Thus, the SVM is trained to predict whether an aneurysm will have ruptured over the specified time interval, given the treatment plan and measured aneurysm characteristics. Once the support vector machine has been trained using the experimentally-obtained training data, it may then be used to predict whether an aneurysm will rupture, given a treatment plan that is under consideration, and given the measured aneurysm characteristics [Christopher J. C. BURGES. A tutorial on support vector machines for pattern recognition. Data Mining and Knowledge Discovery 2(1998), 121-167; J. A. K. SUYKENS, J. Vandewalle, B. De Moor. Optimal Control by Least Squares Support Vector Machines. Neural Networks 14 (2001): 23-35; SAPANKEVYCH, N. and Sankar, R. Time Series Prediction Using Support Vector Machines: A Survey. IEEE Computational Intelligence Magazine 4 (2, 2009): 24-38; Alex J. SMOLA and Bernhard Scholkopf. A tutorial on support vector regression. Journal of Statistics and Computing 14 (3, 2004): 199-222].

Simplification of the training may make use of methods that eliminate consideration of variables that are found to have little effect on the prediction [Felipe ALONSO-Atienza, Jose Luis Rojo-Alvarez, Alfredo Rosado-Muñoz, Juan J. Vinagre, Arcadi García-Alberola, Gustavo Camps-Valls. Feature selection using support vector machines and bootstrap methods for ventricular fibrillation detection. Expert Systems with Applications 39(2012): 1956-1967]. Simplification of the SVM training is accomplished in part by avoiding the use of the raw data, but instead by using features that have been extracted from, or are derived from, the raw data. The derived features are intended to be heuristic and motivated by current knowledge concerning the effects of radiation on a blood vessel and concerning the mechanism by which aneurysms progress towards rupture.

After training the SVM to predict the occurrence of rupture from the other data, success of the SVM is tested with data that were not used for the SVM training. If the success rate is not adequate because it produces too many false positives or negatives, training and testing of the SVM continues until the training is judged to be adequate. At that point, the trained SVM is used to predict whether any potential radiosurgical plan should be eliminated from consideration.

Approving the Planned Radiation Treatment for Delivery

Although much of the planning process is automated, it is understood that the radiosurgeon must ultimately decide whether the plan is reasonable, because no automated process can give unquestionable results, considering the limitations of the data and methods that were used to generate the automated results.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of therapy for a patient, wherein an unruptured brain aneurysm that is not associated with an arteriovenous malformation, not excluding such an unruptured aneurysm that occurs in a blood vessel less than 300 microns in diameter, undergoes a treatment that comprises a noninvasive treatment step wherein an external beam of ionizing radiation is delivered to said aneurysm using stereotactic radiosurgery; wherein the method further comprises formulating a treatment plan that is based in part on a measurement or estimation of a geometric property of the aneurysm of the patient; and wherein said measurement or estimation of the geometric property is made prior to said delivery of radiation to said aneurysm; and wherein the aneurysm has a maximum dimension of less than 5 mm, or wherein the aneurysm has a maximum dimension of between 5 and 10 mm, or wherein the aneurysm has a maximum dimension greater than 10 mm.

2. The method of claim 1 wherein the treatment impedes a natural progression of the aneurysm towards rupture.

3. The method of claim 2 wherein the aneurysm becomes obliterated following the treatment.

4. The method of claim 3 wherein a recurrence of the aneurysm is prevented or delayed.

5. The method of claim 1 wherein the aneurysm is a saccular aneurysm.

6. The method of claim 1 wherein the aneurysm is associated with an artery of the Circle of Willis.

7. The method of claim 1 wherein the aneurysm is not associated with vasculitis, or a vessel to which the aneurysm is attached is not associated with vasculitis.

8. The method of claim 1 wherein the aneurysm did not develop as a consequence of hypertension.

9. The method of claim 1 wherein the aneurysm is not associated with a lenticulostriate vessel.

10. The method of claim 1, wherein the beam of ionizing radiation is produced by a radiation treatment medical apparatus used for stereotactic radiosurgery, or by a stereotactic radiotherapy apparatus comprising a robotic linear accelerator used for a precision delivery of therapeutic x-rays, or by a medical linear accelerator, or by a device that produces a beam of X-rays or gamma rays, or by a device that produces a beam of charged particles.

11. The method of claim 1, comprising formulating an additional treatment plan that is based in part on a measurement or estimation of at least one of the following properties of the aneurysm of the patient: permeability, wall thickness, wall motion, the presence of macrophages, shear stress, and flow velocities; and wherein said measurement or estimation of the at least one property is made prior to said delivery of radiation to said aneurysm.

12. The method of claim 1, wherein the radiation is delivered in one or more fractions.

13. The method of claim 1 wherein the radiation is delivered to only a portion of the aneurysm.

14. The method of claim 1, comprising formulating an additional treatment plan that makes use of a mathematical model that predicts a likelihood of not causing a rupture of the aneurysm.

15. The method of claim 1, wherein the treatment promotes neointimal proliferation and promotes migration of smooth muscle cells or other mural cells, whereby narrowing or occlusion of the aneurysm occurs.

16. The method of claim 1, wherein the treatment promotes a formation of a thrombus.

17. The method of claim 1, and further comprising a step comprising endovascular coil embolization of the aneurysm, wherein said embolization step occurs before or after said noninvasive treatment step wherein an external beam of ionizing radiation is delivered to said aneurysm.

* * * * *